United States Patent
Lathrop et al.

(10) Patent No.: US 10,307,214 B2
(45) Date of Patent: Jun. 4, 2019

(54) MODULAR STERILIZABLE ROBOTIC SYSTEM FOR ENDONASAL SURGERY

(71) Applicant: Vanderbilt University, Nashville, TN (US)

(72) Inventors: Ray Lathrop, Indianapolis, IN (US); Trevor L. Bruns, Nashville, TN (US); Arthur W. Mahoney, Nashville, TN (US); Hunter B. Gilbert, Nashville, TN (US); Philip J. Swaney, Nashville, TN (US); Richard J. Hendrick, Nashville, TN (US); Kyle Weaver, Nashville, TN (US); Paul T. Russell, Nashville, TN (US); Stanley Duke Herrell, Nashville, TN (US); Robert J. Webster, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/360,087

(22) Filed: Nov. 23, 2016

(65) Prior Publication Data
US 2017/0143436 A1    May 25, 2017

Related U.S. Application Data

(60) Provisional application No. 62/258,789, filed on Nov. 23, 2015.

(51) Int. Cl.
| | | |
|---|---|---|
| A61B 34/30 | (2016.01) | |
| A61B 34/37 | (2016.01) | |
| A61B 34/35 | (2016.01) | |
| A61B 90/00 | (2016.01) | |
| A61B 34/20 | (2016.01) | |

(52) U.S. Cl.
CPC ............. *A61B 34/30* (2016.02); *A61B 34/20* (2016.02); *A61B 34/35* (2016.02); *A61B 34/37* (2016.02); *A61B 90/37* (2016.02); *A61B 2034/301* (2016.02)

(58) Field of Classification Search
CPC ... A61B 2034/301; A61B 34/20; A61B 34/30; A61B 34/35; A61B 34/37; A61B 90/37
See application file for complete search history.

(56) References Cited

U.S. PATENT DOCUMENTS

| | | | |
|---|---|---|---|
| 2011/0238083 A1* | 9/2011 | Moll | ......... A61B 8/12 606/130 |
| 2015/0080907 A1* | 3/2015 | Herrell | ......... A61B 19/2203 606/130 |

* cited by examiner

*Primary Examiner* — Muhammad S Islam
(74) *Attorney, Agent, or Firm* — Tarolli, Sundheim, Covell & Tummino LLP

(57) ABSTRACT

A surgical robot system includes a support structure for positioning relative to a patient. The support structure includes a plurality of mounting structures. One or more robotic tool cassettes that are configured to interchangeably connect with any of the mounting structures. Each tool cassette includes a concentric tube manipulator and a transmission for operating the concentric tube manipulator. The support structure also includes a tube collector including a tube assembly associated with each of the mounting structures. The tube assemblies are configured to receive the concentric tube manipulators and guide the manipulators to extend along predetermined trajectories relative to each other.

24 Claims, 20 Drawing Sheets

MODULAR STERILIZABLE ROBOTIC SYSTEM FOR ENDONASAL SURGERY

RELATED APPLICATION

THIS APPLICATION CLAIMS THE BENEFIT of U.S. Provisional Application Ser. No. 62/258,789, which was filed on Nov. 23, 2015. The disclosure of this application is hereby incorporated by reference in its entirety.

GOVERNMENT FUNDING

This invention was made with government support under Grant No. R01 EB017467 awarded by The National Institutes of Health. The United States government has certain rights to the invention.

TECHNICAL FIELD

This invention is related to concentric tube robotic systems for accessing a surgical site through a small incision or natural orifice.

BACKGROUND

Design of surgical robot slave manipulators has recently been moving toward more compact devices, and also away from general purpose robots in favor of systems designed and built with one particular surgical access route or type of surgical procedure in mind. There has also been a trend toward using continuously flexible robots (i.e., "continuum robots") to enhance dexterity inside the patient in small-diameter packages. The requirements of the surgical environment (sterility, ease of use, safety, compactness, etc.) also place stringent design requirements on continuum robot actuation systems.

Endonasal surgical procedures provide a non-invasive approach to addressing the high incidence of disease in the pituitary region of the brain. For example, pituitary tumors account for 15-20% of all primary brain tumors. Conventional transfacial and transcranial surgical procedures offer highly invasive, yet effective, approaches to treating this disease. Treating pituitary tumors using a less invasive endonasal approach can be desirable. This approach, however, can be difficult for a surgeon to execute by hand, due to the confined spaces and the lack of dexterity in current rigid surgical tools, which lack wrists, joints, or other means of controllable deflection. For example, one challenge that can be difficult to overcome with manually operated, rigid endonasal surgical tools is the initial drilling away of bone to enlarge the nasal passage and expose the surgical site, which can be necessary in certain instances.

SUMMARY

According to one aspect, a robotic system can be designed to work with multiple manipulators through the constrained entry point of a smaller natural orifice, such as the nostril. This robotic system can be designed to assist with the initial phase of drilling away the nasal passage. The robotic system can also be deployed to the surgical site to assist with tumor resection and other surgical objectives. The robot's manipulators consist of needle-diameter concentric tube continuum robots, which have dexterity analogous to tentacles. The concentric tube design enables manipulators to be sufficiently small and dexterous that multiple instruments can be inserted and manipulated through a single nostril.

According to one aspect, a surgical robot system includes a support structure for positioning relative to a patient. The support structure includes a plurality of mounting structures. One or more robotic tool cassettes that are configured to interchangeably connect with any of the mounting structures. Each tool cassette includes a concentric tube manipulator and a transmission for operating the concentric tube manipulator. The support structure also includes a tube collector including a tube assembly associated with each of the mounting structures. The tube assemblies are configured to receive the concentric tube manipulators and guide the manipulators to extend along predetermined trajectories relative to each other.

According to another aspect, the support structure can include a main beam and the module mounting structures can be positioned radially about the main beam. The mounting structures can be configured to position the tool cassettes so that the concentric tube manipulators are directed toward a common location.

According to another aspect, the tube collector can be configured to receive and guide the concentric tube manipulators to exit the tube collector at trajectories that are substantially parallel to each other. The tube collector can be configured to redirect the concentric tube manipulators from angled trajectories at which the manipulators are received in the tube collector to substantially adjacent and parallel trajectories at which the manipulators exit the tube collector. In one example configuration, the tube collector can be configured to direct the concentric tube manipulators to exit the tube collecting structure in a pattern configured so that the manipulators can extend through an ellipse having a major diameter of about 14 mm.

According to another aspect, each concentric tube manipulator can include a rigid outer tube and two curved inner tubes. The innermost tube can carry a surgical tool at its tip.

According to another aspect, each of the tool cassettes can share the same form factor and can be interchangeably connectable to the mounting structure.

According to another aspect, each mounting structure can include a carriage assembly configured to receive a tool cassette. The mounting structure can include a motor that is actuatable to move the carriage assembly linearly along the mounting structure to cause gross movement of the concentric tube manipulator of the tool cassette supported by the carriage assembly.

According to another aspect, the carriage assembly can include one or more guide pins configured to be received in corresponding guide holes in the robotic tool cassette. The carriage assembly can also include a handle that is actuatable to engage locking pins on the tool cassette to draw the tool cassette onto the carriage assembly with the guide holes engaging the guide pins. The handle can be configured to lock onto the locking pins to secure the tool cassette on the carriage assembly.

According to another aspect, the guide pins and guide holes can have cross-sectional shapes selected such that a tool cassette having guide apertures of a certain cross-sectional shape can be installed only on carriage assemblies having guide pins configured to be received in those particular guide apertures.

According to another aspect, the carriage assemblies and tool cassettes can share the same form factor so that the tool cassettes can be are interchangeable on the carriage assemblies.

According to another aspect, the concentric tube manipulators of each of the robot module can be adapted to carry a tool at its distal end, such as grippers, surgical lasers, graspers, retractors, scissors, imaging tips, cauterization tips, ablation tips, wrists, curettes, morcelators, knives, scalpels, cameras, irrigation ports, and suction ports.

According to another aspect, the tool cassettes and the concentric tube manipulators can be configured to be sterilizable, and wherein the support structure can be configured to receive a sterile curtain for providing a sterile barrier between the support structure and an operating room environment. The tool cassettes can be constructed of biocompatible and sterilizable components.

According to another aspect, one or more motor packs can be associated with the mounting structures and comprising one or more electric motors configured to supply rotational mechanical power to a tool cassette mounted thereon.

According to another aspect, each tool cassette can include a transmission for providing rotational and/or translational degrees of freedom of movement to the concentric tubes of its associated concentric tube manipulator. The motor pack can include an electric motor dedicated to each degree of freedom provided by the transmission. The motor packs and the tool cassettes can include couplings for automatically coupling the electric motors and the transmission.

According to another aspect, the system can include a protective sleeve for protecting the concentric tube manipulators as they extend from the tool cassettes to the tube collector. The sliding port assembly can be configured to maintain the concentric tube manipulator centered within tubes of the tube collector. The sliding port assembly can be connected to the concentric tube manipulator and configured to arrest advancement of an outer concentric tube with its distal end proximate to and centered within an end portion of the collector tube so that the curved tubes of the concentric tube manipulator exit the tube collector from its center.

According to another aspect, the system can include markers applied to the concentric tubes of the concentric tube manipulator. The markers can be configured to align in a predetermined pattern that is indicative of the concentric tube manipulator being in a home position.

According to another aspect, the tube collector can include an excluder opening through which the curved tubes of the concentric tube manipulator can extend if installed in the tube collector in an improper orientation.

According to another aspect, the tube collector can include an opening through which the curved tubes of the concentric tube manipulator can extend if the tip of the curved tube moves over the opening. The system can be configured to have a homing mode in which the concentric tube manipulator is actuated translationally and rotationally within the collector tube while monitoring the motor currents of motors actuating the concentric tube manipulator. A change in motor current can be indicative of the curved tube tip engaging the opening, which is indicative of the location of the tip in the collector tube.

According to another aspect, the system can include a mechanical latch that locks the tool cassette in a retracted position to prevent re-use of the tool cassette.

DRAWINGS

The foregoing and other features of the invention will become apparent to those skilled in the art to which the invention relates upon reading the following description with reference to the accompanying drawings, in which.

DESCRIPTION

The present invention is related to concentric tube robots or manipulators used to perform surgical operations. More specifically, the present invention is related to surgical systems for implementing one or more robotic concentric tube manipulators for performing surgical operations. In one example implementation, the surgical system can be used to perform endonasal surgical procedures, such as pituitary tumor resection and removal.

The Surgical System

Figure 1:
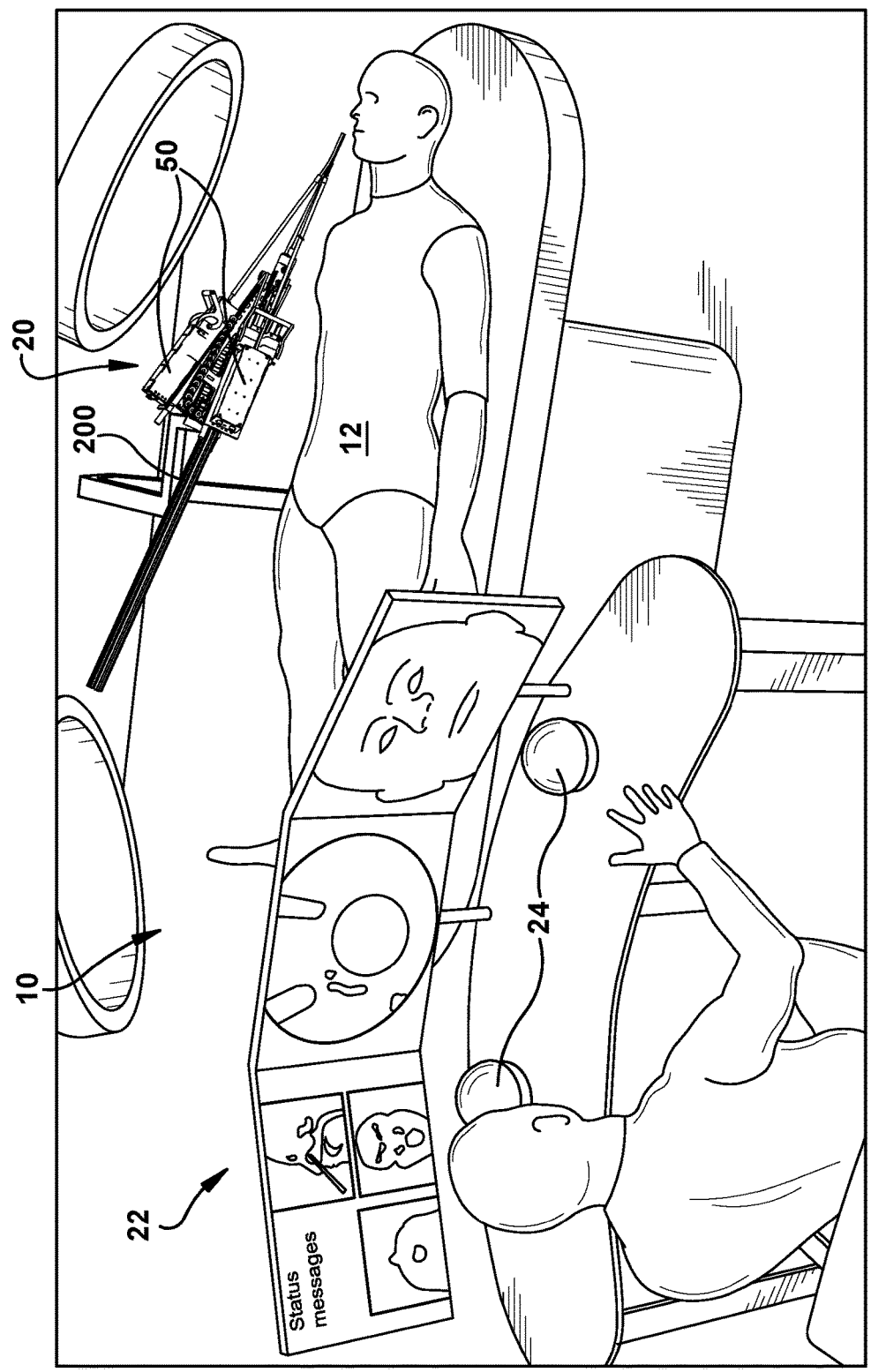
FIG. 1 is an overview of a surgical system according to an example configuration of the invention.

FIG. 1 illustrates an operating room environment in which surgery can be performed and a system 10 for performing a surgical operation on a patient 12. The surgical system 10 illustrated in FIG. 1 is illustrative of a generalized system overview and is not meant to be limiting in terms of system layout, the components included in or excluded from the system, and the configuration of the components included in the system. Instead, the surgical system 10 of FIG. 1 is meant simply to convey by way of one example the general feel for how the surgical system can be implemented.

Figure 2:
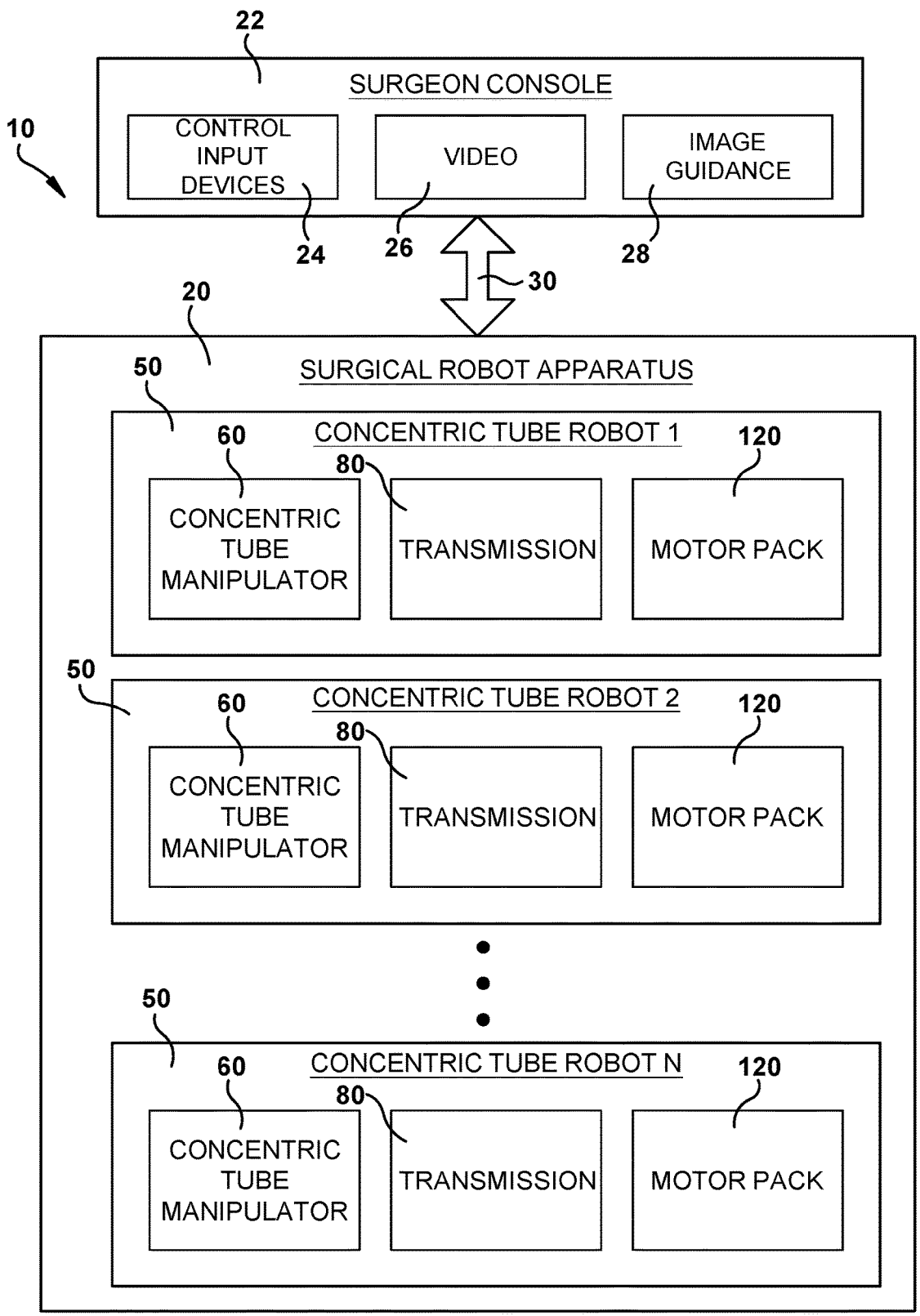
FIG. 2 is a block diagram illustrating components of the system of FIG. 1.
Figure 3:
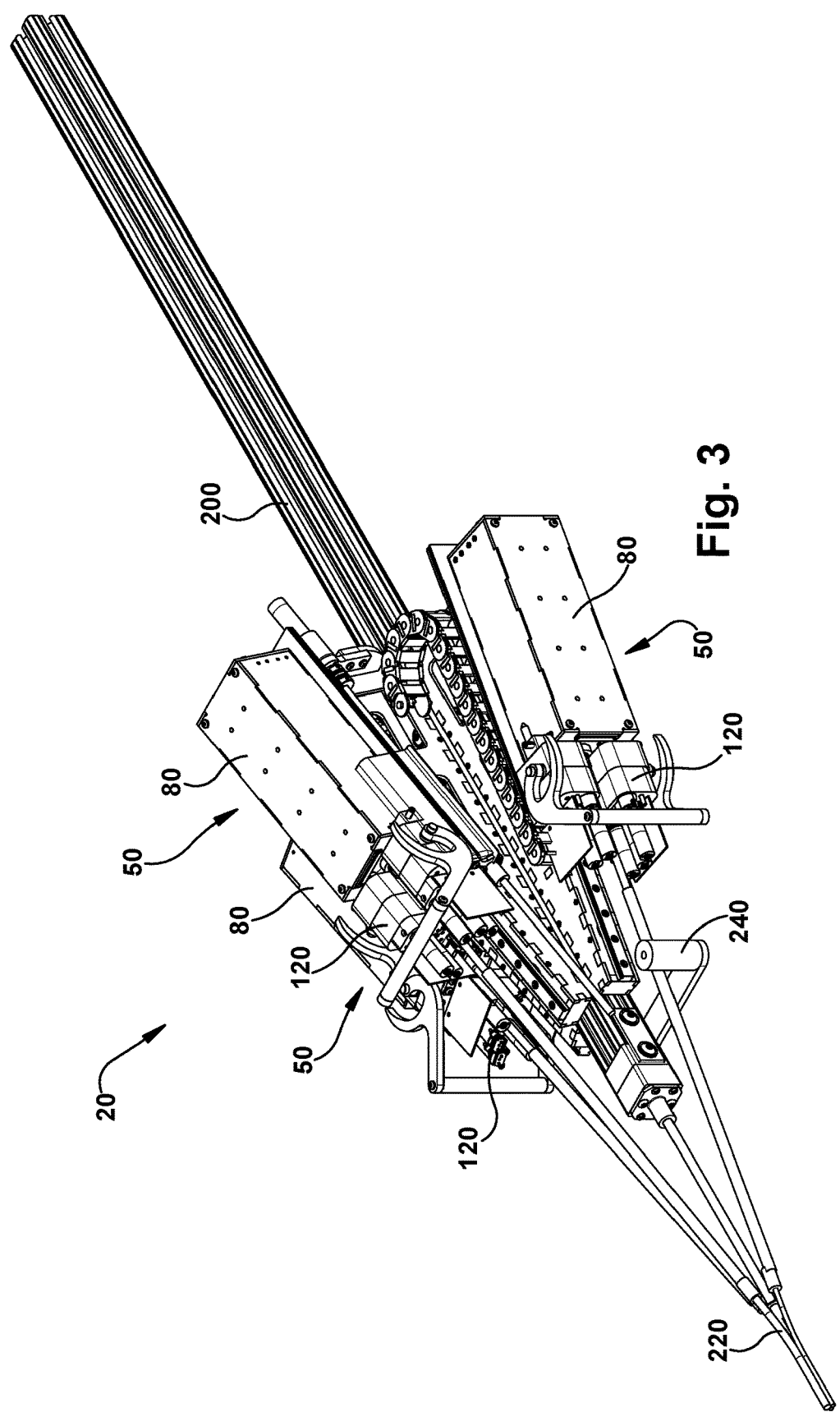
FIGS. 3-5 illustrate a surgical robotic apparatus that can form a portion of the surgical system according to an example configuration of the invention.
Figure 4:
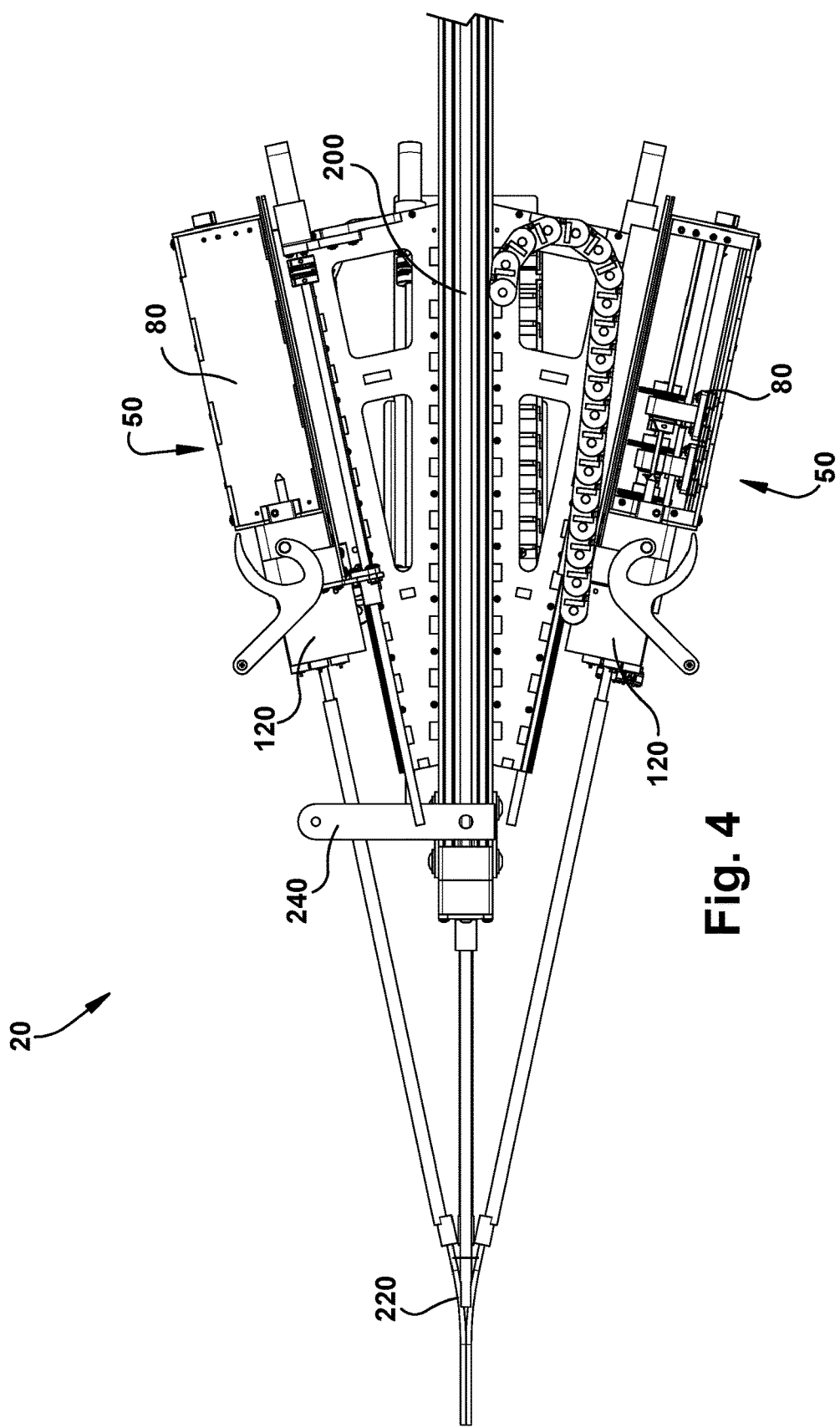

Referring to FIGS. 1 and 2, the surgical system 10 includes a robotic apparatus 20 that can be controlled remotely from a surgeon console 22 to perform a surgical operation. The surgeon console 22 can include control input devices 24, such as haptic controllers, for allowing the surgeon to control the operation (e.g., tele-operation) of the surgical robot 20 while viewing video 26 (such as endoscopic video) and image guidance 28. The surgeon's console 22 includes one or more computers for processing the inputs from the control devices 24 and processing high level control computations for controlling operation of the surgical robotic apparatus 20. The console computers 22 can communicate the high level control signals to the surgical robot apparatus 20 via a suitable connection 30 such as Ethernet.

A video feed from an endoscopic camera can be displayed on the monitors positioned in front of the surgeon. The system is capable of supporting added video overlays, augmenting the video with additional information. In order to reduce video latency, the high definition video signal from the endoscope is read with minimal latency directly into the computer by a frame capture device. The real-time operating system ensures that the frame is displayed within an allotted time.

The surgeon console 22 can include two computers. The first runs a real-time operating system for high-level control of the overall system. It handles the video processing and translates user input into robot commands. These commands are sent to a second computer, also running a real-time operating system, which executes the model-based controller to compute the necessary motor movements. These motions are then sent via Ethernet over the User Datagram Protocol to the low-level motor controller described previously.

To ensure fast transfer of network data with minimal latency, a full-duplex, 20 port, 1 Gb/s Ethernet switch capable of forwarding packets without blocking (Cisco SG-300-20) is used for communication between the system components. This ensures that collisions on the data carrier are not possible, improving determinism. Although we cannot guarantee that the switch provides a hard real-time guarantee, we do note that we measured the forwarding latency of the switch between two network nodes at less than 10 microseconds, indicating that it has minimal impact on the overall system latency.

The surgical robotic apparatus 20 includes structure 200 for supporting one or more concentric tube robots 50. The concentric tube robots 50 are modular in form, and each includes a concentric tube manipulator 60, a transmission 80 for imparting translational and rotational movements to the concentric tube manipulator, and a motor pack 120 including electric motors for supplying power for operating the transmission. The high level control signals are relayed from the console computer 22 to the motor pack 120, which includes low level motor controllers for controlling operation of the electric motors to actuate the transmission 80. The transmission operates to provide the desired response from the concentric tube manipulator 60 and thereby carry out the surgical operation under the remote control of the surgeon from the console 22.

The support structure 200 supports the concentric tube robots 50 in a predetermined orientation so that their concentric tube manipulators 60 are directed angularly relative to each other toward a common point or area at which a tube collector 200 is positioned. The tube collector 200 receives the concentric tube manipulators 60 and redirects them along trajectories that are generally parallel to and spaced closely around a central axis 14 of the robotic apparatus 20. This allows multiple concentric tube manipulators 60 to be delivered through a small incision or orifice and to function in a confined space. For example, the tube collector 200 can facilitate performing an endonasal surgical procedure by focusing multiple concentric tube manipulators 60 through the patient's nose and nasal cavity in order to access the pituitary region of the brain.

Concentric Tube Manipulators

Figure 6:
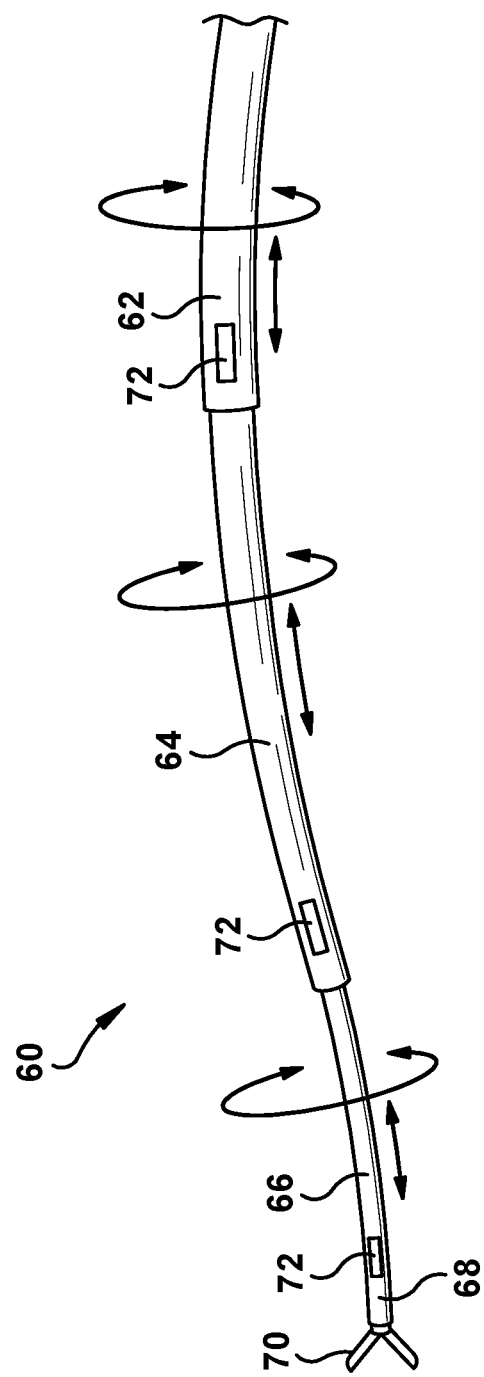
FIG. 6 illustrates a concentric tube manipulator that can form a portion of the surgical robotic apparatus according to an example configuration of the invention.

Referring to FIG. 6, the concentric tube manipulators 60 are small, needle-diameter, tentacle-like robots that include multiple concentric, precurved, elastic tubes. These elastic, curved tubes are typically made of a superelastic metal alloy such as a nickel-titanium alloy ("nitinol") material. The tubes can, individually or in combination, be rotated about the longitudinal axis of the robot and can be translated along the longitudinal axis of the robot. Through translational movement, the tubes can be retracted into one another and extended from one another.

As the precurved tubes interact with one another through relative translational and rotational movement, they cause one another to bend and twist, with the tubes collectively assuming a minimum energy conformation. The precurvature(s) of the tube(s) for a given manipulator 60 can be selected to provide a desired workspace throughout which the tip can access. The curved shape of the distal end of the manipulator 60 is controlled via translation and rotation of each tube at a proximal location (e.g., at its base) outside the patient. The concentric tube manipulators 60 are particularly well suited to natural orifice procedures because their small diameter and remote actuation enable them to operate in areas where bulkier actuation systems (e.g., tendons and pulleys) are not feasible. The size of the manipulator 20 is limited only by the size of nitinol tubes available, which can be an outer diameter of as little as 200 μm or less.

Distal ends of the manipulators 60 carry surgical tools. In FIG. 6, the distal end of the manipulator 60 carries grippers 70. The manipulator 60 could, however, carry alternative tools, such as surgical lasers, graspers, retractors, scissors, imaging tips (e.g., endomicroscopy, optical coherence tomography (OCT), spectroscopy), cauterization tips, ablation tips, wrists (for dexterity), curettes, morcelators, knives/scalpels, cameras, irrigation ports, and suction ports.

The concentric tube manipulator 60 includes three concentric tubes: an outer tube 62, a first inner tube 64, and a second, or innermost, inner tube 66 with a tip 68 that carries the grippers 70. The outer tube 62 can translate axially and rotate; the first inner tube 64 can translate axially and rotate; and the second inner tube 66 can translate axially and rotate. The translational movement of each tube 62, 64, 66 is indicated generally by its associated straight arrow in FIG. 6. The rotational movement of each tube 62, 64, 66 is indicated generally by its associated curved arrow in FIG. 6. The concentric tube manipulator 60 thus has six degrees of freedom (DOF)—rotational and translational degrees of freedom for each of three tubes. The concentric tube manipulator 60 can be made to have any desired number of degrees of freedom, for example, by adding/removing tubes and/or by limiting the degrees of freedom of one or more tubes to translational only or rotational only.

All three tubes 62, 64, 66 of the concentric tube manipulator 60 can be curved such that they follow a predetermined curved path. The tubes 62, 64, 66, if retracted into a straight rigid tubular structure, will conform to that straight structure. As the tubes 62, 64, 66 are extended, i.e., translated, out of the rigid structure, the nitinol tubes will re-assume their predefined curved configuration due to their inherent superelastic shape memory properties. In one example configuration, the outer tube 62 of the concentric tube manipulator 60 can be a straight, stiff tube made, for example, of stainless steel and used to provide translational and rotational movement without any curvature. In this configuration, the straight outer tube 62 can be relatively rigid so that the curved inner tubes 64, 66 that it carries will conform and straighten when retracted therein.

In describing the unique characteristics of the curved concentric tube manipulators 60 described herein, it should be noted and understood what is meant by the terms "axis"

or "axial" used in conjunction with the manipulators. Because the curved tubes are coaxial in nature, the axis of the manipulators 60 themselves can be considered to be centered within and follow the curved configuration of the manipulators. Thus, as the curved configuration of the manipulator 60 changes, the axis remains centered in the tubes and follows. However, in this description, reference is also made to rotation of the manipulators 60 and to rotation of the individual concentric tubes that make up the manipulators. In this description, rotation of the manipulators 60 or of any of the concentric tubes that make up the manipulators is meant to refer to rotation about a straight portion of the manipulator proximal to the associated transmission 80 that imparts that rotation to the tube. Thus, as the manipulator 60 rotates, the straight portions of the concentric tubes rotate about a common central axis (i.e., coaxially) whereas the curved portions of the tubes move about that same straight linear axis.

The curved tubes 62, 64, 66, when extended, will resume their precurved configurations due to their superelastic material construction. By controlling the relative translational and rotational positions of their respective tubes, the tip 68 of the concentric tube manipulator 60 can be maneuvered to any position within the workspace defined by the characteristics of the particular tubes. Thus, through careful selection of the tubes used to construct the manipulator 60, their respective workspaces can be tailored to suit the particular surgical task and the physiology of the patient environment in which the task is performed.

Robot Transmission

Figure 5:
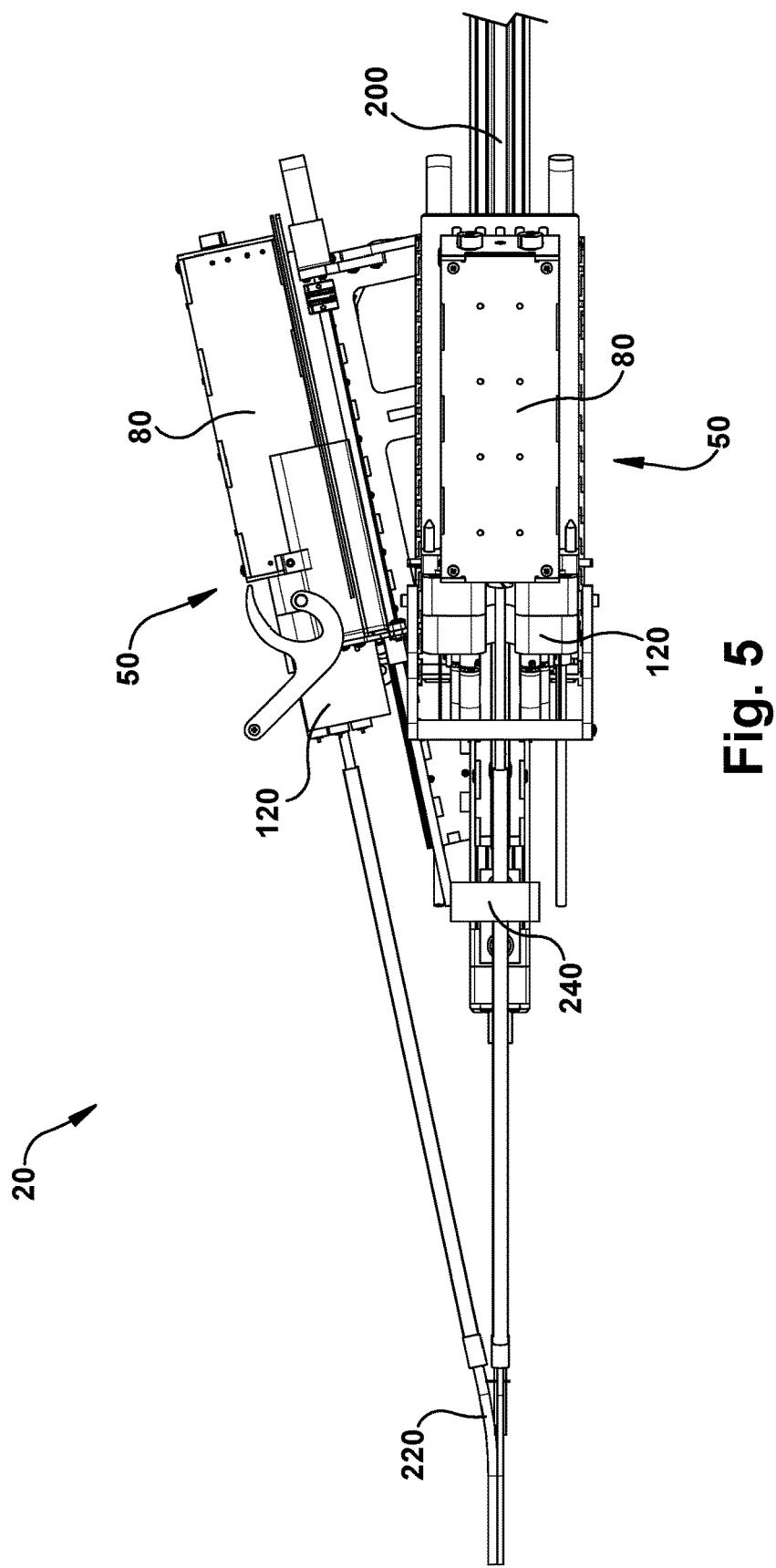
Figure 7:
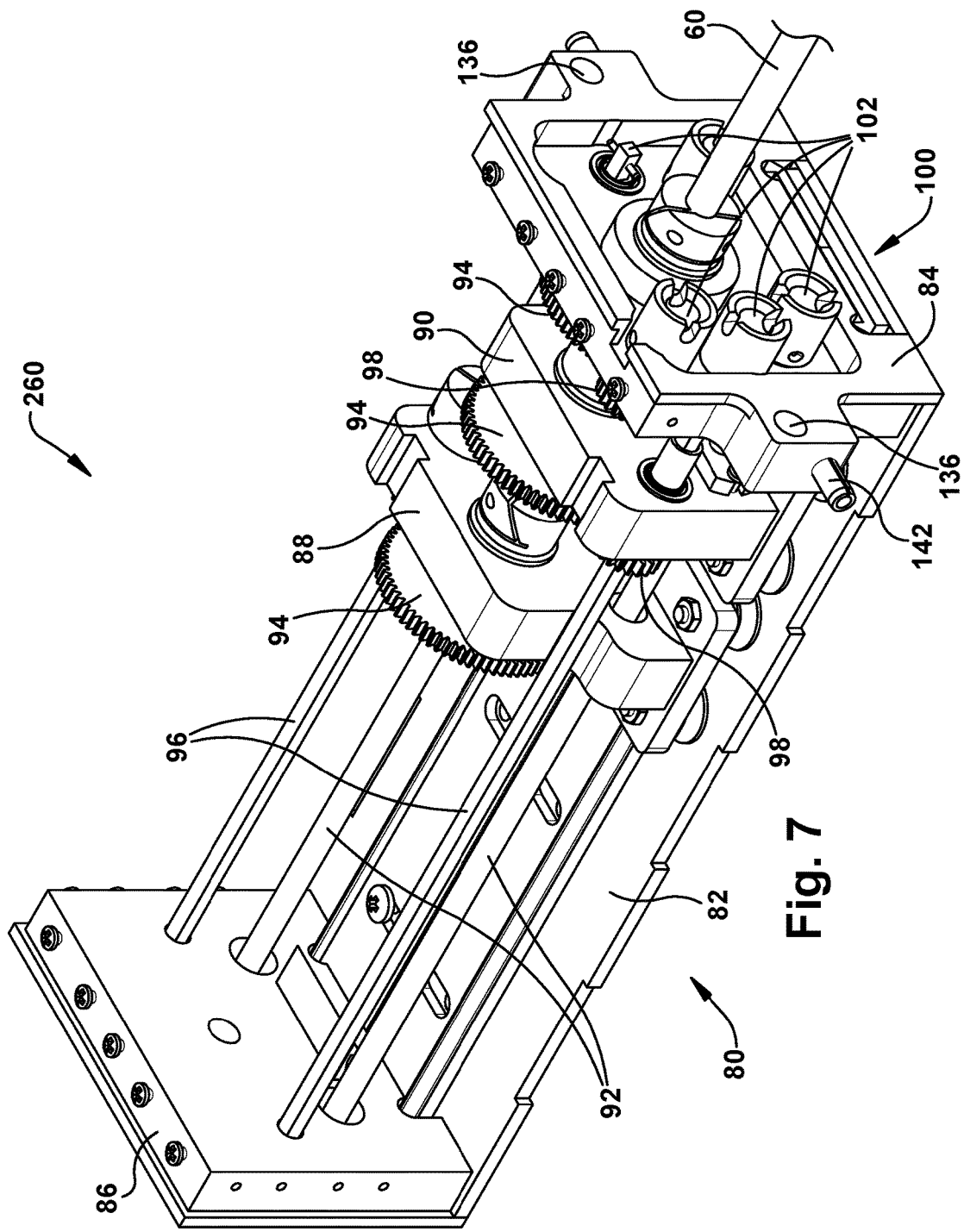
FIGS. 7-9 illustrate a transmission that can form a portion of the surgical robotic apparatus according to an example configuration of the invention.
Figure 8:
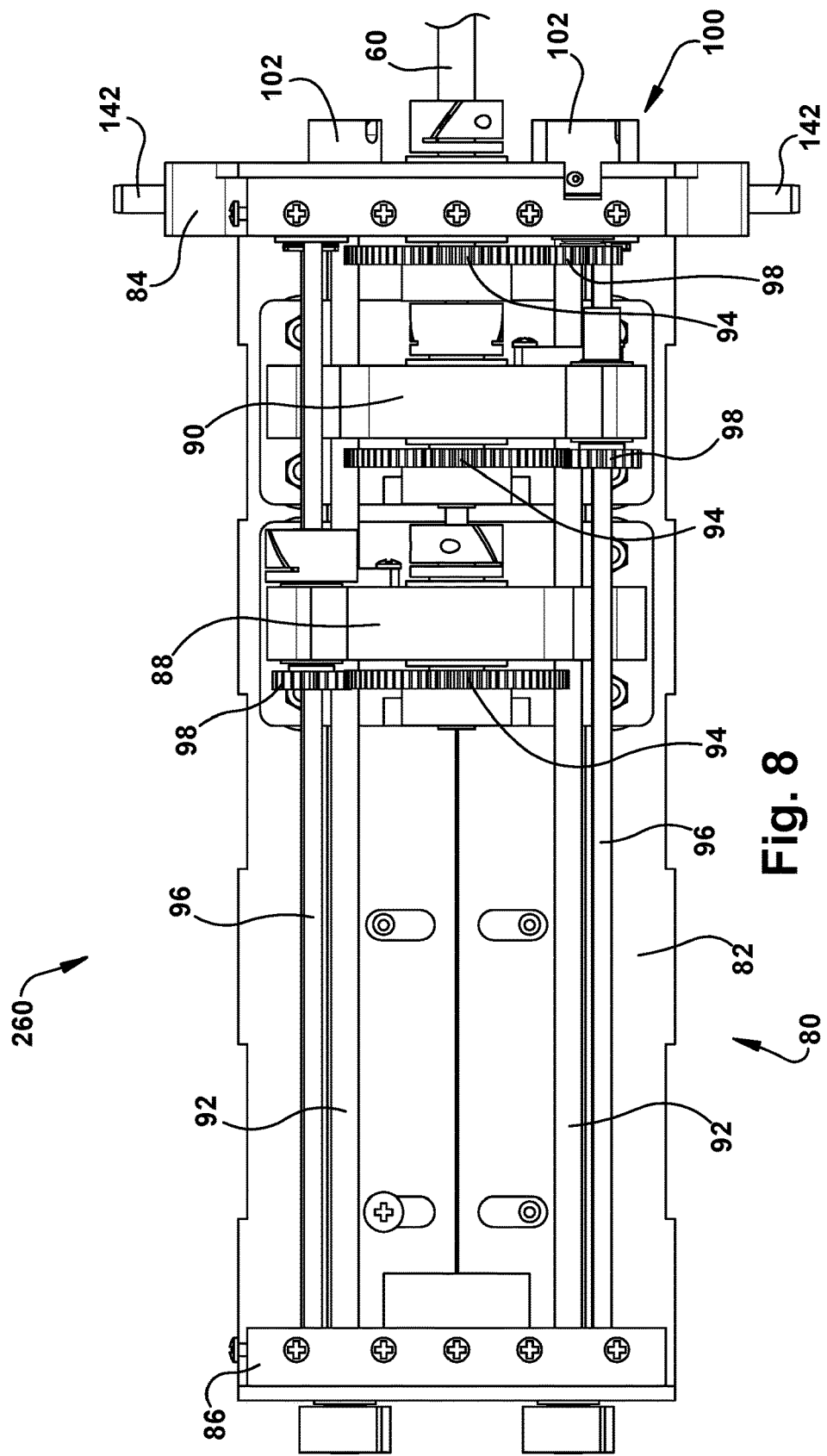
Figure 9:
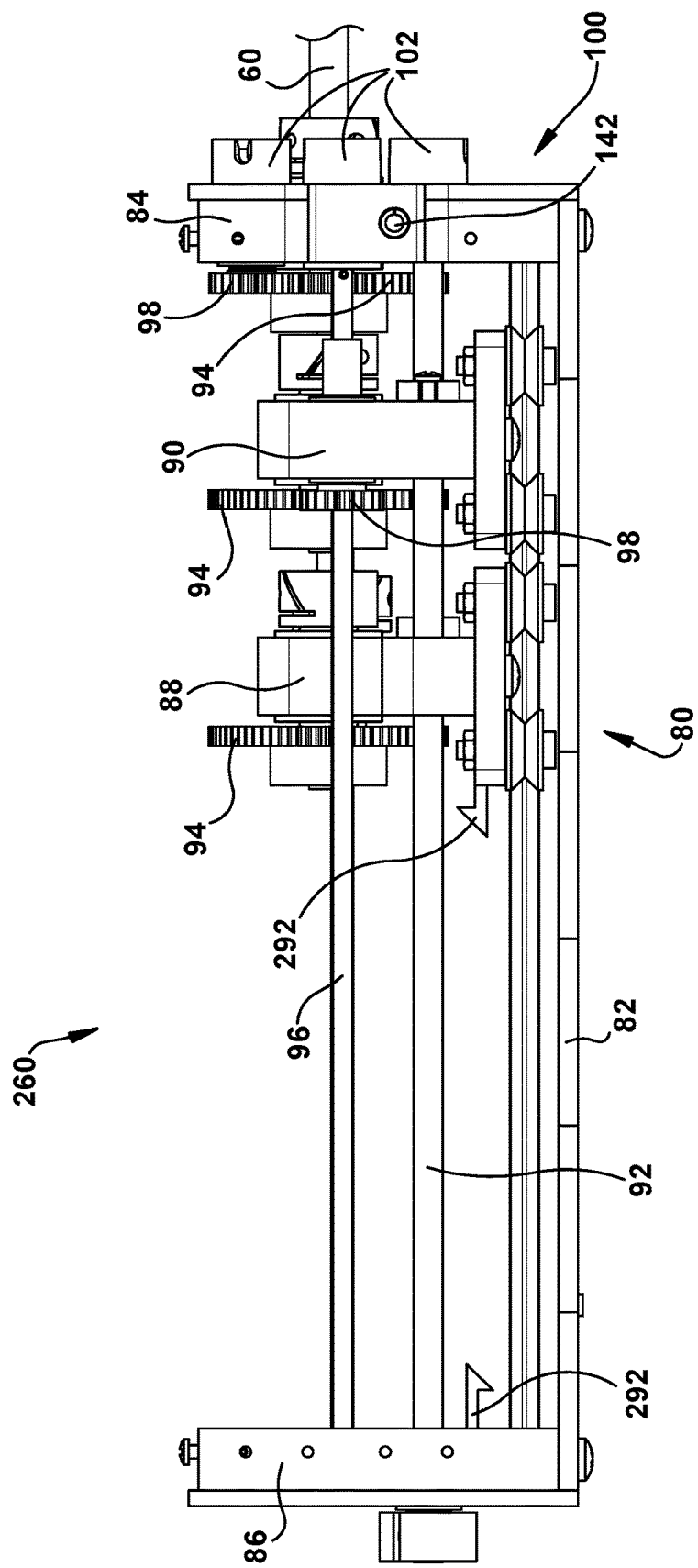

Referring to FIGS. 7-9, the transmission 80 of the robot 50 includes a frame 82 that supports a front end plate 84 and a rear end plate 86. The transmission also includes a plurality of tube carriers, one associated with a tube of the associated concentric tube manipulator 60 for which translation and/or rotation is to be imparted. In the example configuration of FIG. 5, the transmission 80 includes two tube carriers: a first tube carrier 88 proximate the rear end plate 86, and a second tube carrier 90 proximate the front end plate 84. In order for a variety of different sized tools to exit from a standard cassette design, the front plate 84 can include an adjustable aperture that is able to accommodate the full range of expected tool diameters.

The tube carriers 88, 90 can move linearly along the length of the frame 82 in response to rotation of respective screw drives 92. The first inner tube 64 (which is not visible in FIGS. 7-9) moves linearly with the first tube carrier 88. The second inner tube 66 (also not visible in FIGS. 7-9) moves linearly with the second tube carrier 90. The linear motion of the rube carriers 88, 90 thus provides the translational movement of the inner tubes 64, 66. Translational movement of the first inner tube 64 is imparted through rotation of the screw drive 92 associated with the first tube carrier 88. Translational movement of the second inner tube 66 is imparted through rotation of the screw drive 92 associated with the second tube carrier 90.

Each tube carrier 88, 90 includes a geared tube holder 94 that is rotatable in response to rotation of an associated rotation shaft 96 which rotates a drive gear 98. Rotation of the tube holders 94 produce rotation of the concentric tube associated with the tube carrier 88, 90. Thus, rotation of the first inner tube 64 is imparted by rotation of the rotation shaft 96 associated with the tube holder 94 of the first tube carrier 88. Rotation of the second inner tube 66 is imparted by rotation of the rotation shaft 96 associated with the tube holder 94 of the second tube carrier 90.

Rotational movement of the outer tube 62 of the concentric tube manipulator 60 is imparted by a geared tube holder 94 that is secured to or proximate the front end plate 84. Rotation of the tube holder 94 associated with the outer tube 62 is imparted by rotation of an associated drive gear 98. Translational movement of the outer tube 62 can be imparted through linear movement of the entire transmission 80 relative to the support structure 200 itself, which is described below.

The robot 50 in the example configuration of FIGS. 7-9 thus includes a three tube concentric tube manipulator 60 including the outer tube 62 and the first and second inner tubes 64, 66. The robot 50 is therefore a six degree of freedom robot, providing translational and rotational movement of all three concentric tubes 62, 64, 66.

From the above description, it will be appreciated that each tube carrier 88, 90 is configured to impart translational movement of its associated manipulator tube via rotation of the associated drive screw 92, and to impart rotational movement of its associated manipulator tube 64, 66 via rotation of the associated rotation shaft 96. For translational movement, the tube carrier 88, 90 moves linearly along the length of the transmission frame 82, driven by the drive screw 92, and carrying with it the associated manipulator tube 64, 66. For rotational movement, the tube holder 94 rotates, driven by gears through rotation of the rotation shaft 96, and the associated manipulator tube 64, 66 rotates with it. Rotation of the outer tube 62 is imparted by rotation of the associated rotation shaft 96, and translation of the outer tube 62 is imparted through translation of the transmission 80 itself. In this configuration, not only is the outer tube 62 translated, the entire concentric tube robot 60 is translated as well. Thus, it will be appreciated that translation of the transmission 80 itself can be done to insert and retract the associated concentric tube manipulator from the surgical site.

The transmission 80 also includes a motor pack interface 100, which can be connected to or formed as a part of the front end plate 84. The motor pack interface 100 is configured to receive and connect with a motor pack 120 (described below) that is used to impart rotation to the drive screws 92 and rotation shafts 96. As such, the motor pack interface 100 includes a plurality of drive couplings 102. Each drive coupling 102 is associated with a respective one of the drive screws 92 or rotation shafts 96.

FIGS. 7-9 illustrate just one example configuration of the transmission 80. The transmission 80 can, however, have various configurations suited to produce rotational and translational movement of the concentric tube manipulator. For example, the transmission 80 can be similar or identical to the transmission described and illustrated in U.S. patent application Ser. No. 14/256,540, filed Apr. 18, 2014, which is published as U.S. Patent Publication U.S. 2015/0080907 A1, the disclosure of which is hereby incorporated by reference in its entirety.

Motor Pack

Figure 10:
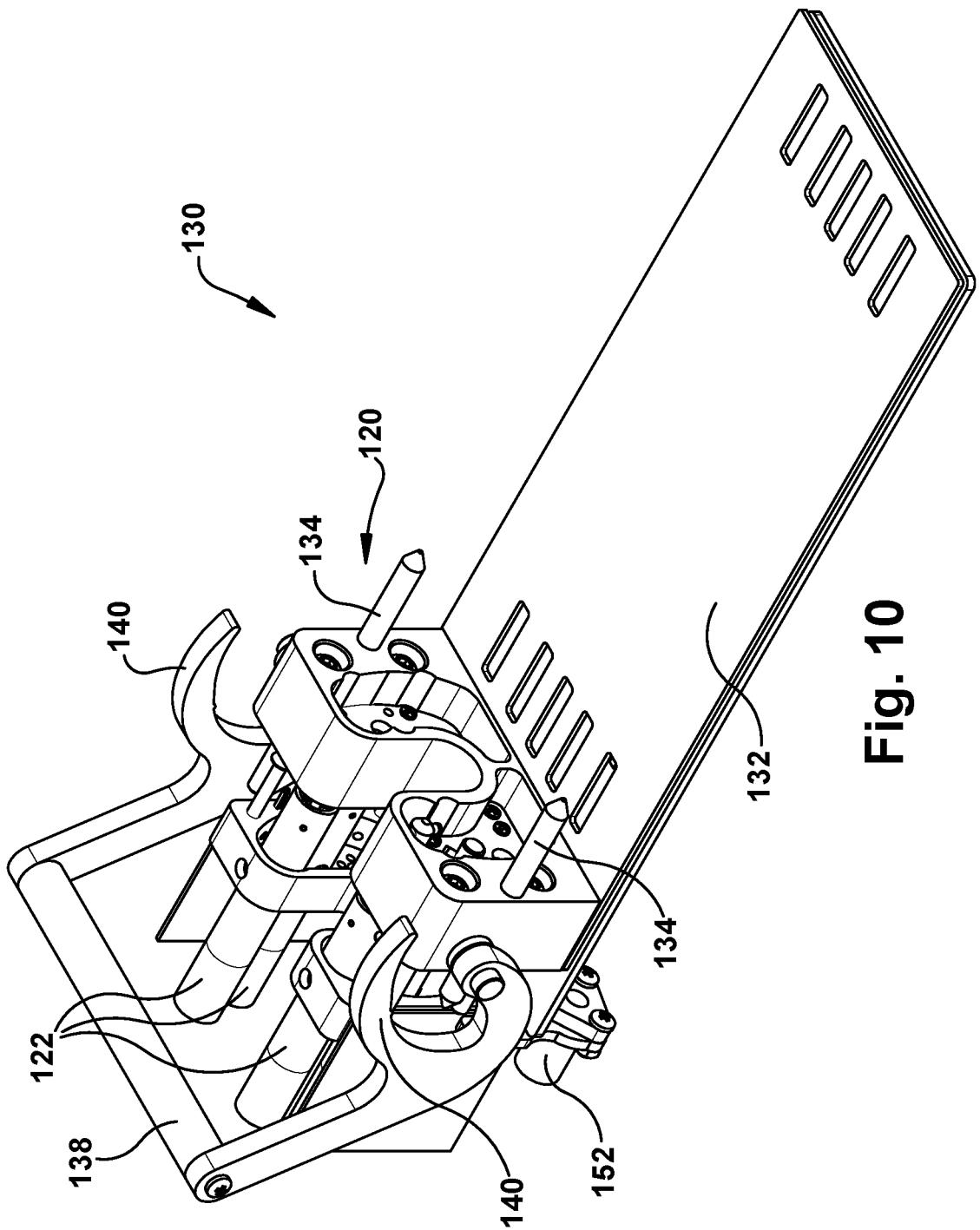
FIGS. 10-12 illustrate a carriage assembly that can form a portion of the surgical robotic apparatus according to an example configuration of the invention.
Figure 11:
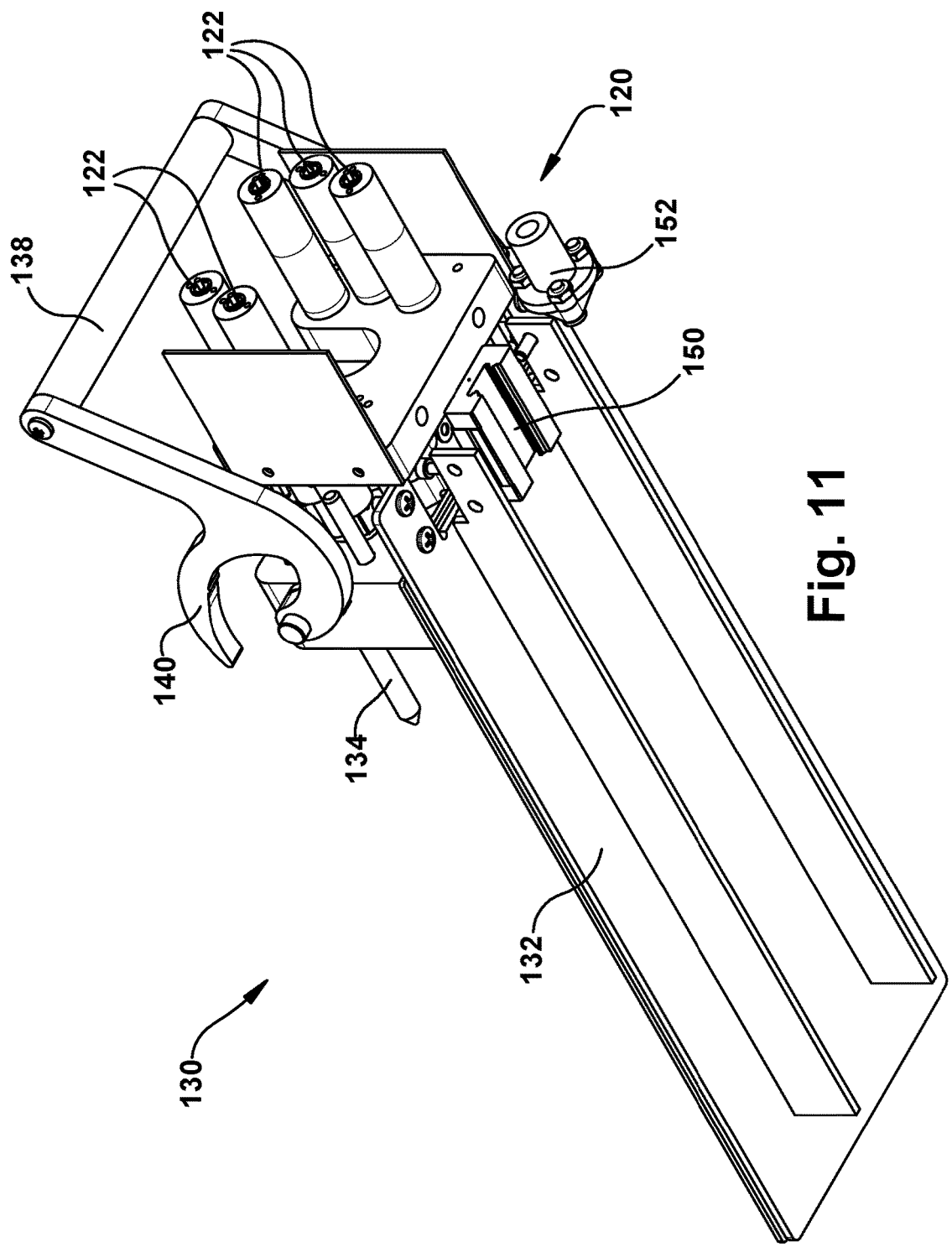
Figure 12:
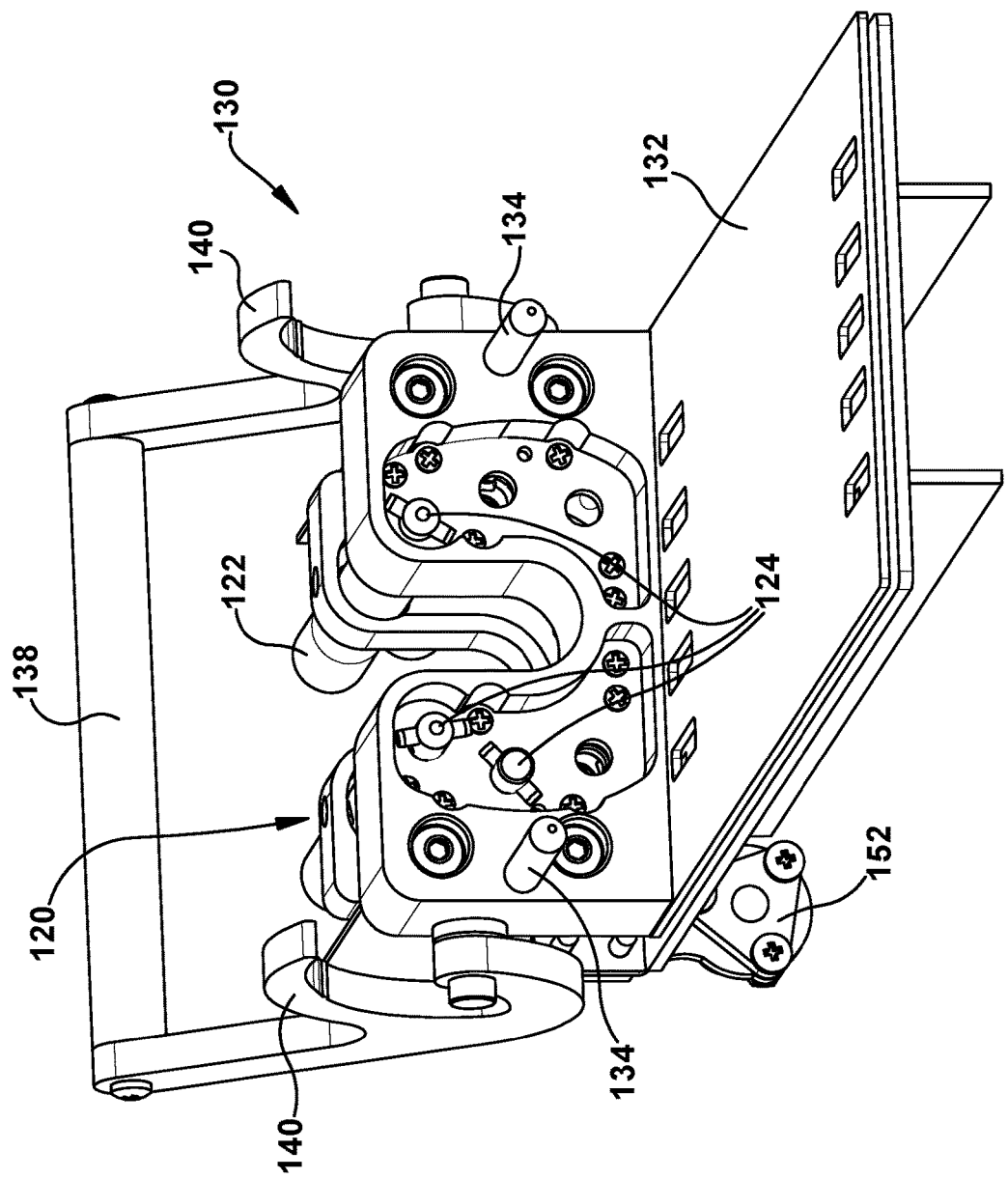

Referring to FIGS. 10-12, the motor pack 120 is formed as a portion of a carriage assembly 130 of the robotic surgical apparatus 20. The carriage assembly 130 is connectable to the support structure 200, which is described in further detail below. The carriage assembly 130 is configured to receive, connect with, and support the transmission 80. To facilitate this, the carriage assembly 130 includes a base plate 132 upon which the transmission 80 can be positioned. The carriage assembly 130 includes guide pins 134 that are received in corresponding guide apertures 136 in the front plate 84 of the transmission 80. A handle 138 pivots relative to the carriage 130 and include locking hooks 140 that engage corresponding locking pins 142 of the transmission 80. Rotating the handle 138 toward the transmission 80 resting on the base plate 132 causes the hooks 140 to engage the locking pins 142. The locking pins 142 slide along the hooks 140, which act as cam surfaces that pull on the locking pins 142 and pull the transmission 80 toward the motor pack 120. The handles 138 lock the transmission 80 onto the carriage assembly 130.

The motor pack 120 includes a plurality of motors 122, each of which includes a drive coupling 124. As the handle locks the transmission 80 onto the carriage assembly 130, the guide pins 134 guide the transmission 80 so that the drive couplings 102 of the transmission motor interface 100 engage the drive couplings 124 of the motor pack 120. The motor drive couplings 124 mate with the transmission drive couplings 102 so that operation of the motors 122 causes rotation of its associated drive screw 92/rotation shaft 96. The motors 122 of the motor pack 120 can thus be operated to control actuation of the concentric tube manipulators 60 via operation of the transmission 80. In doing so, each motor 122 is associated with one degree of freedom of the concentric tube manipulator 60. Therefore, the degrees of freedom of the robot 50 can be controlled individually through actuation of the motors 122. It therefore follows that, for the six DOF robot 50 of the example embodiment, the motor pack 120 would include six motors 122.

In the illustrated example configuration, the drive couplings 102, 124 have a male/female configuration. In the example configuration illustrated in FIGS. 10-12, the transmission drive couplings 102 are female couplings including a cylindrical shroud with radially opposed slots. The motor drive couplings 124 have a clevis pin configuration in which the coupling component that rotates with the motor shaft includes a transverse hole through which a cross-pin extends. This cross pin is received in the slots of the transmission drive couplings 102 to transmit torque from the motor pack 120 to the transmission 80. To facilitate easy installation of the transmission 80 on the carriage assembly 130, one or both of the transmission and motor drive couplings 102, 124 can be movable axially against the bias of a spring so that the couplers can compensate for some misalignment during engagement. Additionally, the location of the male and female couplings can be swapped, so that the transmission drive coupling is male and the motor drive coupling is female.

Alternative connectors can be used to form the drive couplings 102, 124. For example, Oldham couplings, which are well known in the art as being shaft couplings that are simple, secure, reliable, and that allow for some misalignment in the shafts. In this configuration, for instance, each transmission drive coupling 102 can include a slotted female coupler, and each motor drive coupling 124 can include tabbed male coupler. To facilitate easy installation of the transmission 80 on the carriage assembly 130, one or both of the male and female couplers can be movable axially against the bias of a spring so that the couplers can compensate for some misalignment during engagement.

In one example configuration of the motor pack 120, the motors 122 can be brushless motors (e.g., Maxon USA) due their power/weight ratio. Each motor 122 can include a 2000 count/rev encoder and a planetary gear head. Due to the large quantity of motors required (28 motors for a four robot implementation), custom motor control boards handle the low-level control of the robot. Each of five identical 'motherboards' contain sockets for up to six 'daughterboards', which control a single motor each. The motherboards can contain an ARM® Cortex®-M4 microcontroller (e.g., Teensy 3.1, PJRC, USA), which receive commands from the high-level controller over the communication (e.g., Ethernet) network. The microcontrollers parse these commands to update a closed-loop PID controller running at 1 kHz. A 16-bit digital-to-analog converter (DAC) is used to proportionately control the electric current output of the motor amplifiers (e.g., µZ Servo Drive, Advanced Motion Controls, USA). Motor position is monitored with quadrature decoders (e.g., LSI7366, LSI Computer Systems Inc., USA). Digital communication among these peripherals can be accomplished via SPI protocol.

Support Structure

Figure 13:
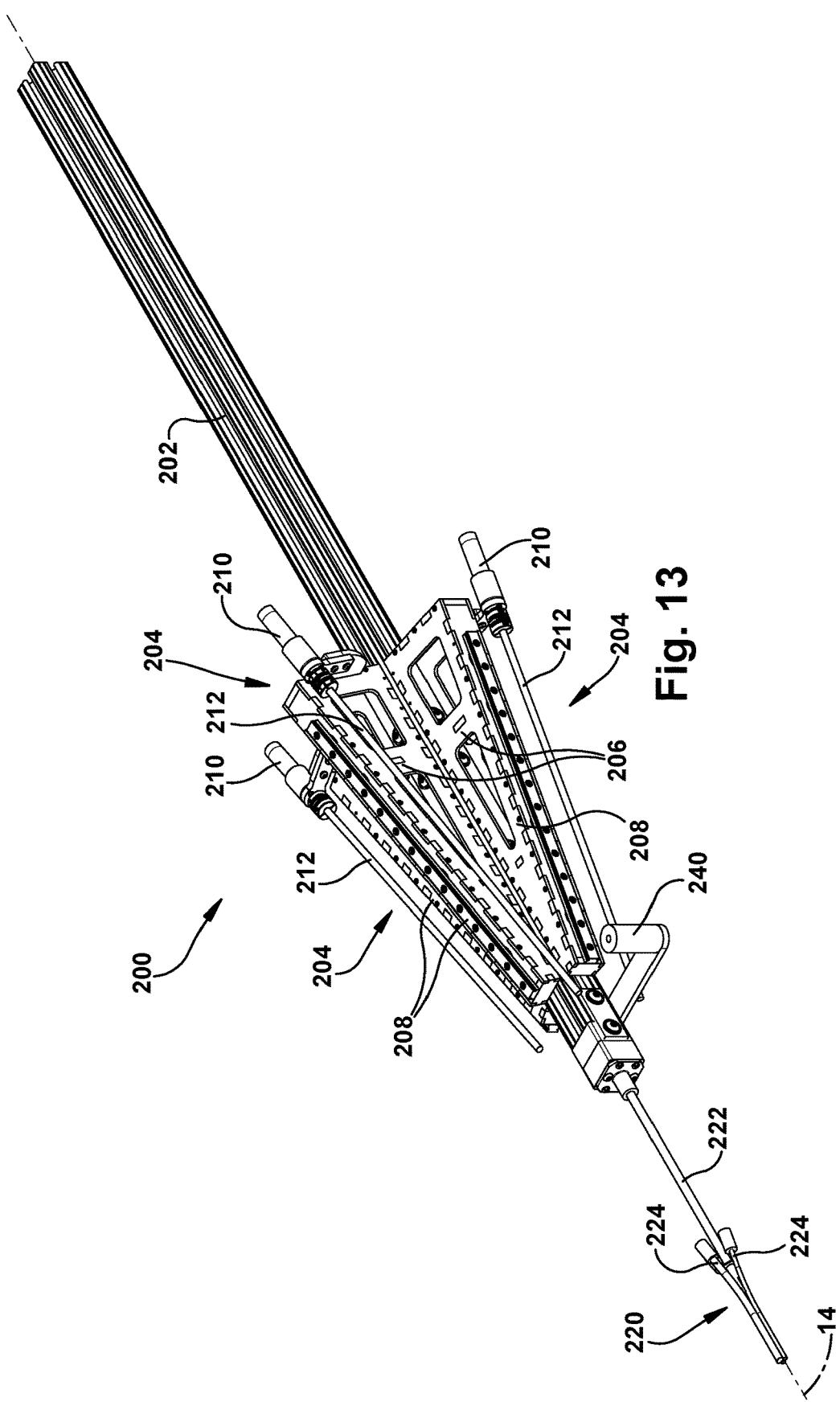
FIGS. 13 and 14 illustrate a support structure that can form a portion of the surgical robotic apparatus according to an example configuration of the invention.
Figure 14:
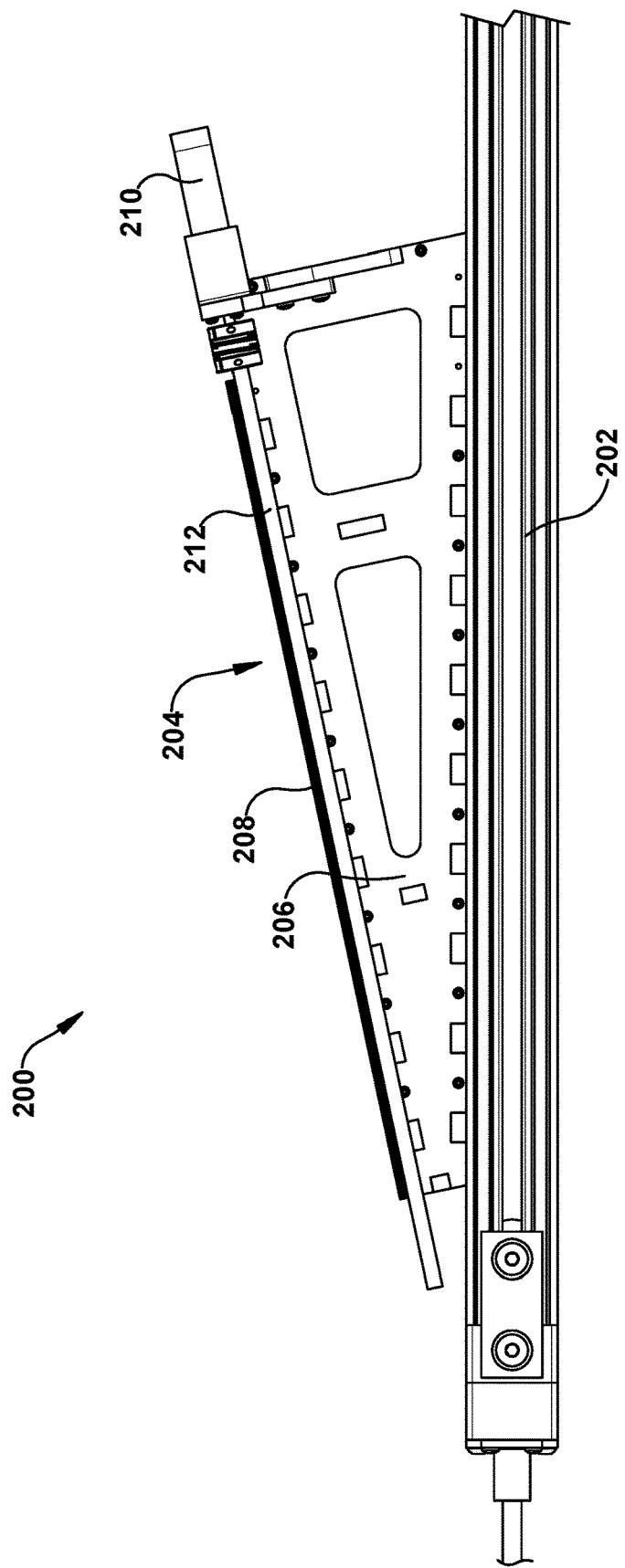

Referring to FIGS. 13 and 14, the support structure 200 includes a main beam 202 that serves as the primary support for the surgical robot apparatus 20. The main beam 202 can have a channeled configuration in which multiple channels can receive mating connectors to facilitate both supporting the main beam (and the surgical robot apparatus 20) itself and supporting structures from the main beam. In the example configuration of FIGS. 13 and 14, the main beam 202 can be generally square in cross-section and thus can have a have four longitudinal channels—one on each side. Through these channels, the main beam 202 can be adapted to cooperate with rigid mounting structures, such as racks or stands, to support the surgical robot 20 in the operating room environment.

The main beam 202 can support one or more robot mounting structures or robot mounts 204. Each robot mount 204 includes a support plate 206 that is received in a beam channel and a rail 208 that caps a longitudinal edge of the support plate. The support plates 206 have generally triangular configurations in which the rails 208 extend at an angle relative to the axis 14. The angles at which the rails 208 extend can be directed toward a common point or area in space along the axis 14. The rails 208 have a cross-sectional configuration that mates with a slider 150 on the underside of the carriage 130 (see FIG. 11). The slider 150 fits onto the rail 208 in a sliding engagement in which the carriage 130 can travel linearly along the angled rail.

Each robot mount 204 also includes a motor 210 that operates a drive screw 212. The drive screw 212 can be received in a threaded receiver 152 on the carriage 130. The motor 210 is operable to rotate the drive screw 212 which urges the carriage 130 and its associated concentric tube robot 50 to travel longitudinally along the rail 208 of the robot mount 204. This longitudinal movement of the carriage 130 and associated robot 50 supplies the translational movement of the outer tube 62 specifically, and the concentric tube manipulator 60 generally. The motor 210, drive screw 212, and receiver 152 thus supply a degree of freedom (the sixth degree of freedom in the example embodiment) of the concentric tube robot 50.

The surgical robotic apparatus 20 also includes a tube collector 220. Each tube collector 220 includes a support post 222 that is secured to an end of the main beam 202 and extends from the main beam along the axis 14. The tube collector 220 also includes one or more tube assemblies 224 that are positioned about the axis 14. Each tube assembly 224 includes a funnel fitting 226 fitted onto an end of a tube 228. In the example embodiment, the tubes 228 are bent tubes. The tubes could have alternative configurations, such as straight tube configurations. The purpose of the tube assemblies 224 is to receive the concentric tube manipulators from their angled trajectories coming from the robots 50 mounted on the robot mounts 204 and re-direct the tubes to extend parallel or substantially parallel and adjacent to the axis 14. The tube collector 220 can direct the concentric tube manipulators 60 to exit the tubes in a compact pattern. For example, for an endonasal application, the exit pattern of the tube collector 220 can be an ellipse having a major diameter of about 14 mm or so.

Figure 15:
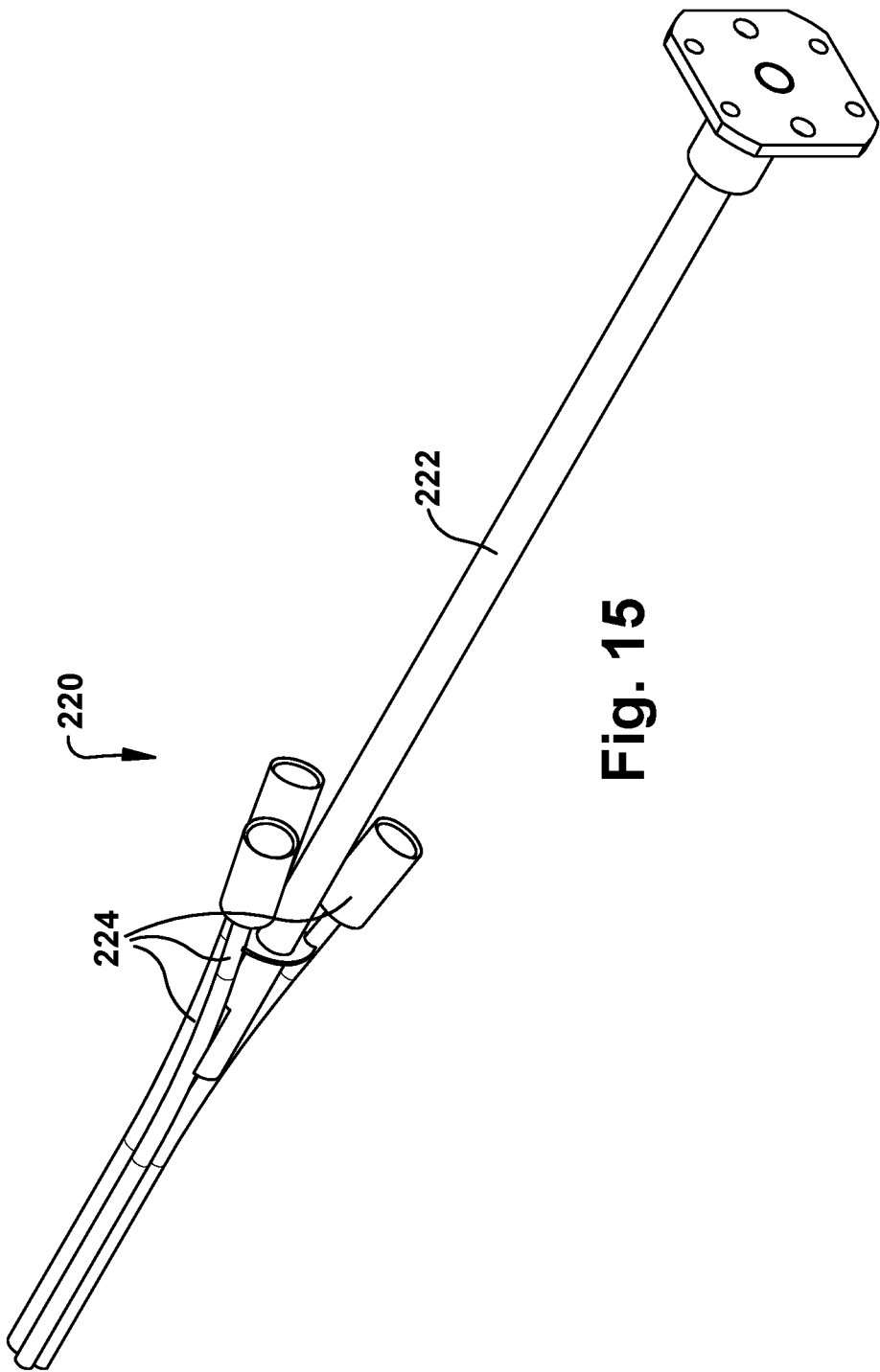
FIGS. 15-17 illustrate a tube collector that can form a portion of the surgical robotic apparatus according to an example configuration of the invention.
Figure 16:
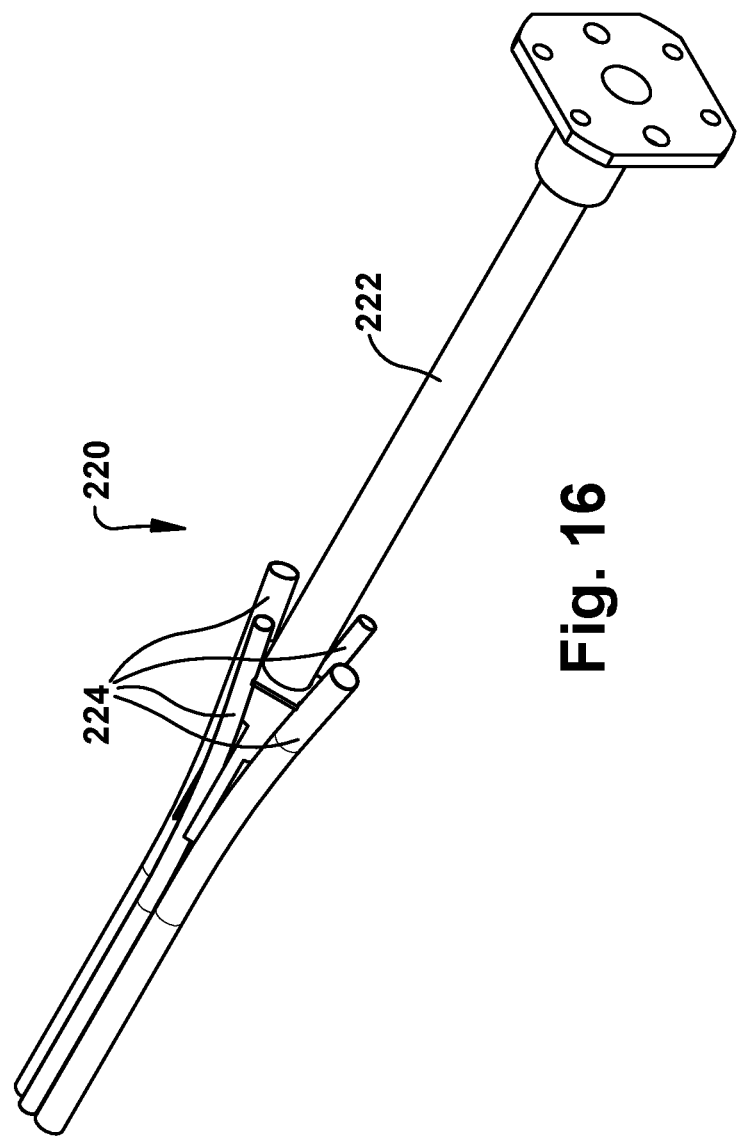
Figure 17:
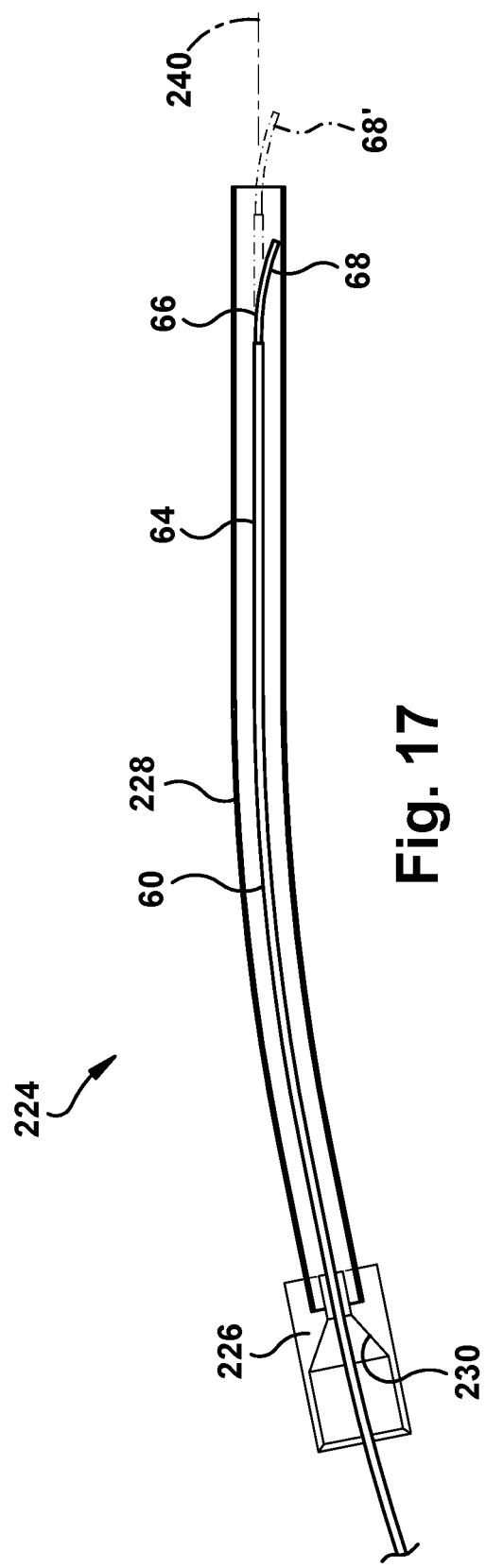

Examples of nose assemblies 220 that can be connected to the main beam 202 of the support structure 200 are illustrated in FIGS. 15 and 16. FIG. 15 illustrates a three-tube tube collector 220 including three tube assemblies 224. FIG. 16 illustrates a four-tube tube collector 220 including four tube assemblies 224. Referring to FIG. 17, the funnel fittings 226 of the tube assemblies 224 have a conical inner surface 230 for directing the concentric tube manipulators 60 of the robots 50 into the bent tube 228.

The support structure 200 can also include an endoscope mount 240 that is secured to the main beam 202 adjacent or near the tube collector 220. The endoscope mount 240 can support an endoscope structure (not shown) which can be used to direct a camera device, such as an optical fiber, into one of the tube assemblies 224 of the tube collector 220. In this instance, for example, the robot apparatus 20 can include three robots 50 and can be fit with the four-tube tube collector 220 of FIG. 16. This way, the robots 50 can occupy three of the tube assemblies 224 and the endoscope/camera can occupy the fourth tube assembly.

Robot Biocompatibility

The support structure 200, transmission 80, concentric tube manipulators 60, and tube collector 220 can be designed to be both sterilizable and biocompatible, constructed entirely from autoclavable and biocompatible components. For example, the materials used to construct these components can be either biocompatible polymers (e.g., Ultem® or PEEK®), stainless steel (which would be passivated before clinical use), aluminum (which would be anodized before clinical use), or nitinol (in the case of the concentric tube manipulators 60). Certain connections between the components can be achieved using a biocompatible and autoclavable bonding agent or glue (e.g., Loctite®, M-21 HP medical device epoxy agent). All of these materials can withstand sterilization in an autoclave.

Figure 18:
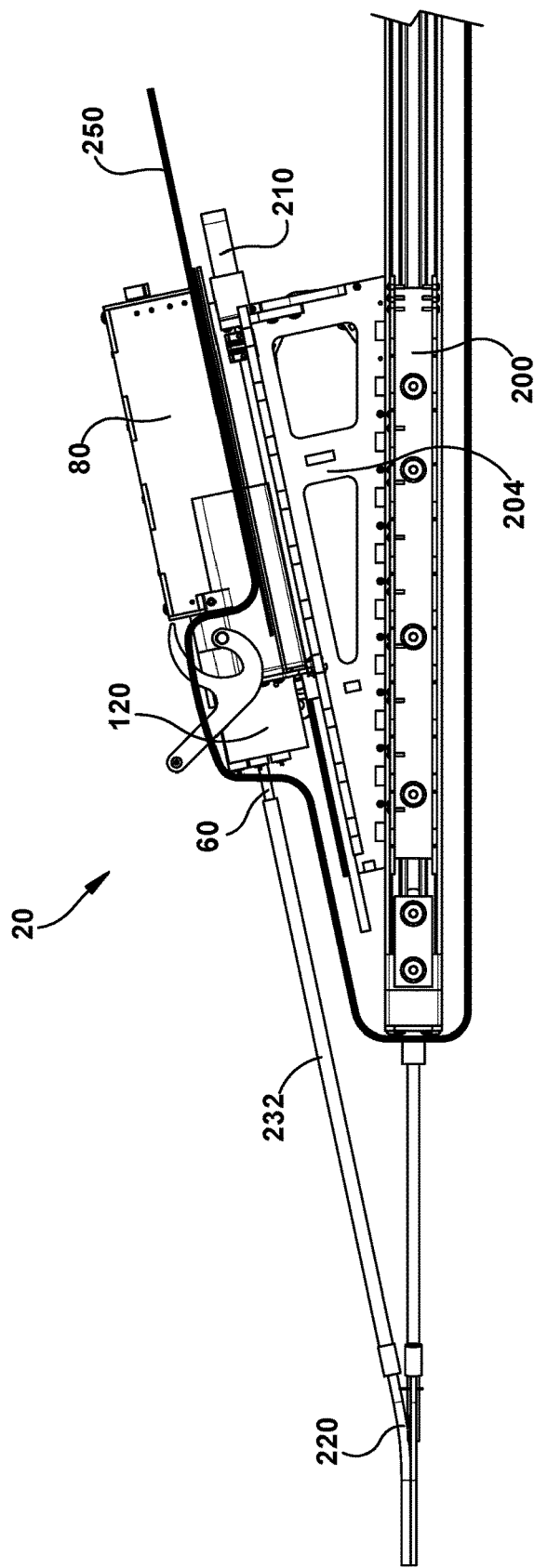
FIG. 18 illustrates a sterility feature that can form a portion of the surgical robotic apparatus according to an example configuration of the invention.

For example, referring to FIG. 18, a sterile curtain or bag 250 can be used to isolate the components of the surgical robotic apparatus 20 that are either too large to be autoclave sterilized (such as the support structure 200) or that cannot withstand autoclave sterilization (such as the motor packs 120). The sterile bag 250 encloses the non-sterilizable components, including the support structure 200, motor pack 120, robot mount 204, and robot mount motor 210 from the surgical environment.

Modular Design

Complex assembly of concentric tube manipulators can be cumbersome and undesirable in a surgical environment. Loading these surgical tools, especially while wearing gloves, should be simple and not require any fine motor skills. Advantageously, the surgical robotic apparatus is configured so that the transmission 80 and the concentric tube manipulator 60 connected thereto can act as a tool cassette 260 (see FIGS. 7-9) that is easily installed, simply by actuating the handle 138 on the carriage 130. By pre-configuring tool cassettes 260 to include the desired transmission 80 and concentric tube manipulator 60 combinations prior to the surgical operation, the tool cassettes 260 necessary to complete the operation can be hot-swapped on an as-needed basis. Advantageously, since the transmissions 80 and concentric tube manipulators 60 are sterilizable, the sterile bag 250 need not be disturbed while swapping the pre-sterilized tool cassettes 260.

The modularity provided by the tool cassettes 260 allows the surgical robotic apparatus 20 to be adapted to custom arrangements or varying tool combinations. For example, skull-based procedures may require the use of two graspers/manipulators, a suction/irrigation device, and a camera. Each would be located at the distal end of a concentric tube device and can be delivered by the surgical robot apparatus fit with a four tube collector 220. These tools could be pre-loaded on transmissions 80 to form cassettes 260 that can be installed and swapped as necessary.

To help facilitate the different tool configurations of the cassettes 260, the surgical robotic apparatus 20 can also include protective sleeves 232 that enclose and protect the concentric tube manipulators 60 as they are directed toward the funnel fittings 226 of the tube assemblies 224. It is the protective sleeves that are received by funnel fittings 226 so that the concentric tube manipulators 60 can be fed through the bent tubes 228. The protective sleeves 232 help account for different tool diameters of the concentric tube manipulators 60 and differences in their diameters and the diameter of the tube assemblies 224. The protective sleeves 232 can accept any tube diameter up to a specified value, enabling a variety of tools to be used with a single standardized cassette design.

Advantageously, the cassettes 260 are identical and can be docked into any available tool carriage 130. Installation of the cassettes 260 requires no tools. Rather, the large handle 138 is simply rotated to lock the cassette 260 in place. A tapered fit between guide pins 134 and mating holes 136 ensures proper alignment. This can allow for tool selection based on the particular procedure for which the robotic apparatus 20 is being used.

For example, in an endonasal procedure, in order to deploy four surgical tools through a single nostril, the concentric tube manipulators 60 should be as close together as possible at the deployment point. For the average female, this is around 300 mm². Therefore, the nose assemblies 220 can be configured to occupy an area of less than 200 mm² in order to help ensure that the robot 20 will be compatible with as many subjects as possible.

One potential issue that could arise in the modular approach involves the initial insertion of the concentric tube manipulators 60 into the tube assemblies 224. Referring to FIG. 17, even though the funnel fittings 226 include the conical surface 230 for directing the concentric tubes 64, 66 toward the center of a smaller diameter bent tube 228, the concentric tubes still can be substantially smaller in diameter than the bent tube. This size differential is necessary due to the need to accommodate various sizes of the concentric tubes 64, 66 and end effectors. As a result of the bent tube 228 being larger in diameter than the concentric tube manipulator 60, and due to the tendency of the concentric tubes to assume their curved configurations, the tubes 64, 66 could curve while within the bent tube 228. As a result, the tip 68 of the concentric tube manipulator 66 could deviate from the bent tube axis 240 while within the tube 228, as indicated generally at 68 in FIG. 17. This is opposed to the desired trajectory, indicated generally at 68' in FIG. 17, in which the concentric tube manipulator 60 follows the bent tube axis 240 and exits the bent tube centered upon that axis.

Due to the need for the tube assembly 224 to accommodate concentric tube manipulators 60 of varying diameters, reducing the diameter of the bent tube 228 is not a desirable solution. One option to address this situation could be the addition of an external aperture (similar to a collet or lens aperture) mounted to the end of the nose tube. It is opened to allow passage of the end effector and cannula during loading/removal and then closed down to support the cannula during use. This can be unnecessarily complicated, however, especially when the small diameters and their necessitating the manipulation of small parts are considered.

Alternatively, the surgical robotic apparatus 20 can include a sliding port assembly that serves as an adapter for mating the concentric tube manipulator 60 to the tube assembly 224. This is illustrated in FIGS. 19A-19D. The sliding port assembly 270 includes a sliding tube 272 that has a diameter selected to mate with and closely fit within the protective sleeve 232. The sliding tube 272 has an end fitting 274 that secures the sliding tube to the concentric tube manipulator 60. The sliding port assembly also includes a diameter adapter 276 that is also secured to the concentric tube manipulator 60 at a position that is spaced forward of the end fitting 274. The diameter adapter 276 has a diameter that is selected so as to have a clearance with the protective sleeve 232 and the funnel fitting 226 so as to pass easily through both structures. The diameter of the diameter adapter 276 is also selected to mate with and slide within the bent tube 228.

Figure 19A:
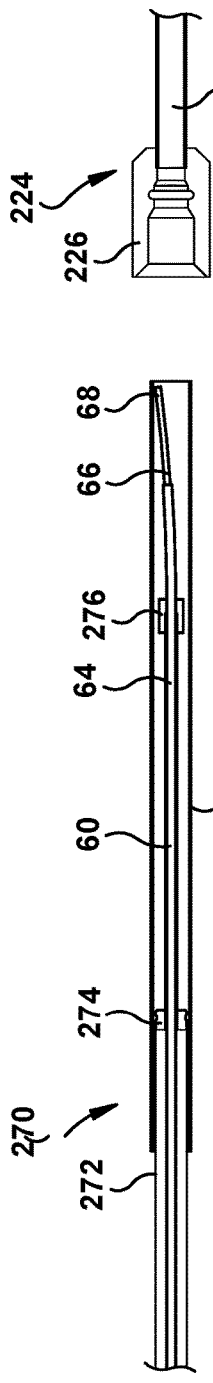
FIGS. 19A-19D illustrate a sliding port assembly that can form a portion of the surgical robotic apparatus according to an example configuration of the invention.
Figure 19B:
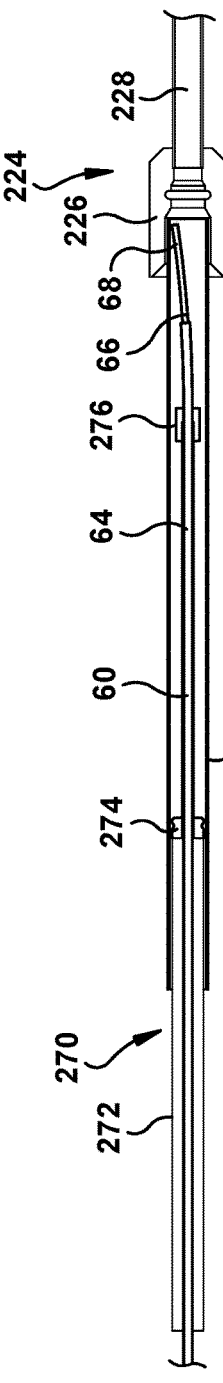

Referring to FIG. 19A, the concentric tube manipulator 60, with the sliding port assembly 270 fixed thereto, is inserted into the protective sleeve 232. The concentric tube manipulator 60 is inserted until the tip 68 is proximate the end of the protective sleeve 232. Referring to FIG. 19B, the assemblage of the protective sleeve 232, concentric tube manipulator 60, and sliding port assembly 270 is directed into the funnel fitting 226 of the tube assembly 224. The protective sleeve 232 is received and retained within a collar portion of the funnel fitting 226.

Figure 19C:
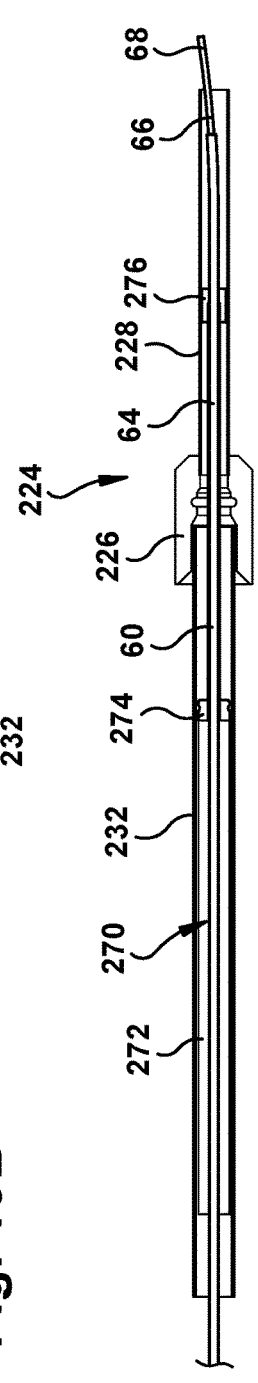

Referring to FIG. 19C, the concentric tube assembly 60 and the sliding port assembly 270 are advanced within the protective sleeve into the tube assembly 224. The funnel fitting 226 guides the tip 68 of concentric tube 66 into the bent tube 228. Eventually, the diameter adapter 276 passes through the funnel fitting 226 and enters the bent tube 228. While this occurs, the end fitting 274 of the sliding tube 272 advances toward the funnel fitting 226.

Figure 19D:
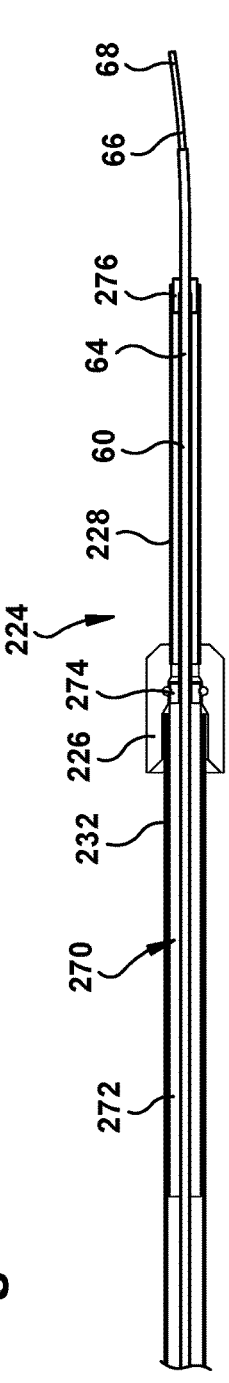
Figure 20A:
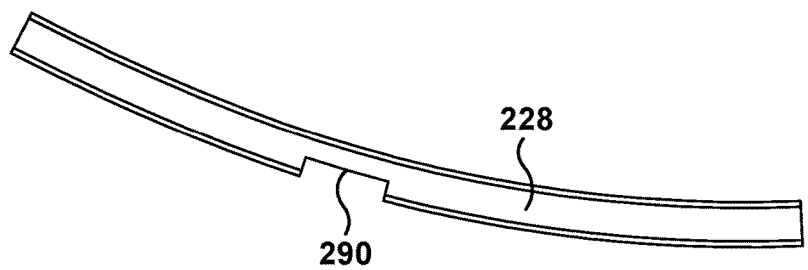
FIGS. 20A-20C illustrate a safety feature that can be implemented in the surgical robotic apparatus according to an example configuration of the invention.
Figure 20B:
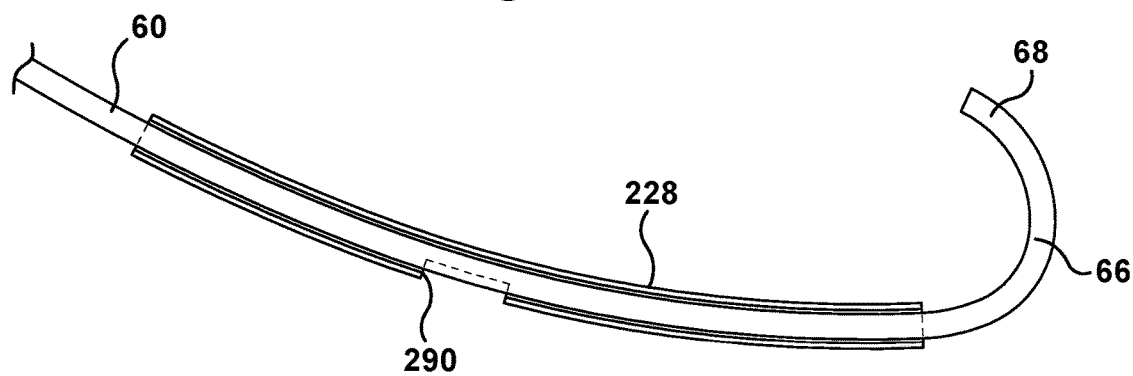
Figure 20C:
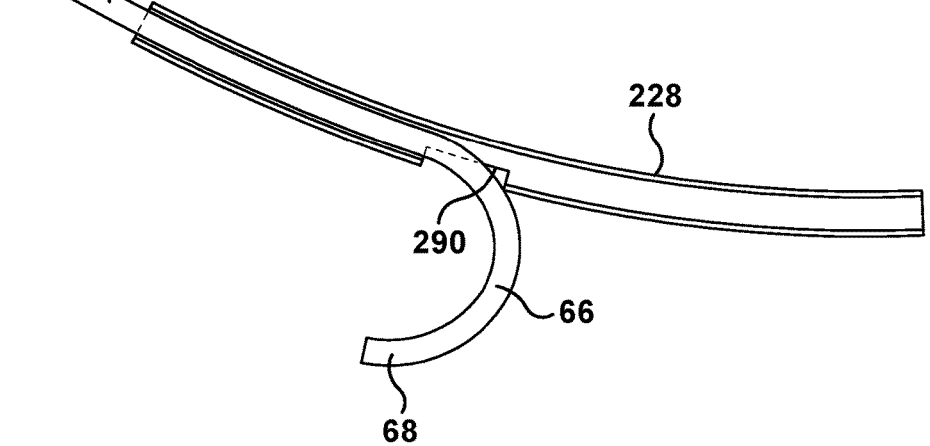

Referring to FIG. 19D, the end fitting 274 eventually reaches and enters the funnel fitting 226. The funnel fitting 226 can include a retaining feature 280, such as an annular groove, that receives a retaining feature 282 of the end fitting 274, such as an annular ridge. The end fitting 274 can be constructed of a resilient deformable material, such as rubber, that allows the retaining feature 282 to compress, enter the retaining feature 280, and expand to lock or retain the end fitting in the funnel fitting 226.

Advantageously, the diameter adapter 276 can be spaced a predetermined distance from the end fitting 274 so that the diameter adapter is positioned at the distal end of the bent tube 228 when the end fitting locks into the funnel fitting 226. This way, as shown in FIG. 19D, the diameter adapter 276 can direct the concentric tube manipulator 60 to exit from the bent tube 228 from a position centered within the tube.

Additional Features

Another aspect of the surgical system 10 implementing the robotic surgical apparatus 20 is the need to "home" the concentric tube manipulator 60. Homing the concentric tube manipulators 60 registers the orientation and translation of the concentric tubes relative to the robot system. One method for performing this is illustrated in FIG. 6. According to this feature, each tube 62, 64, 66 of the concentric tube manipulator 60 can include a marker 72 that can be identified and located by a sensing device, such as a camera or an electromagnetic sensor. In one example configuration, the marker 72 can be an optical marker, such as an infrared (IR) reflective marker, that can be identified by an IR camera of the surgical system 10. In another example configuration, the markers 72 can be magnetic and sensed by a Hall sensor. In a further example configuration, the markers 72 can be reflective and sensed by reflecting a transmitted light or laser beam back to a receiver. Alternatively, the metal structure of the concentric tubes could reflect the transmitted light or laser beam to the receiver and the markers 72 could be non-reflective so that their location is identified by breaking the light/laser beam. In a homing procedure, the robot 50 can be operated to line up the markers 72 both rotationally and translationally to a desired home location.

To ensure that the concentric tube robot 60 is properly homed in the robotic surgical apparatus 50 prior to performing a surgical operation, the tube assembly 224 can be configured to include a safety feature. Referring to FIGS. 20A-20D, the tubes 228 can include an excluder opening 290 in the tubular sidewall. The excluder opening 290 can be configured to occupy a predetermined radial segment of the tube 228 so that a concentric tube manipulator 60, if properly oriented or homed, will pass through the tube with the bent tip 68 of the tube 66 engaging a portion of the tube radially adjacent or opposite the excluder opening. An improperly homed or oriented concentric tube manipulator 60 will have its tip 68 engage and pass through the excluder opening 290 thus preventing its use.

Advantageously, the excluder opening 290 can also be used for homing the concentric tube manipulator 60 without the aid of the markers 72 described above. To do this, the curved concentric tube could be moved within the tube 228 of the collector 220 until the tip 68 of the curved tube 66 pops through the excluder opening 290. At this point, a spike in motor current would be realized by the controller due to the increased resistance of the concentric tubes engaging the edges of the excluder opening 290. The control system could then move the concentric tube manipulator back and forth in both linear and angular degrees of freedom to seek the midpoint of the resistance in both degrees of freedom, as indicated by measured motor current values. This identified resistance midpoint can be used to home the concentric tube manipulator 60. Once the midpoint is identified, the system 20 can be configured to home the concentric tube manipulator 60 either at that location or at a location that is determined based on that location.

As another feature, the tool cassettes 260 could be disposable, in which case the surgical robotic device 50 could include a single use limiting feature. According to this feature, as shown in FIG. 9, the transmission 80 could include a latch mechanism in which a latch element 292 fixed to the first tube carrier 88 can engage a mating latch element 294 on the rear plate 86 when the first tube carrier carries the concentric tube manipulator 60 to the retracted position after use. The latch mechanism would prevent any further use of the transmission 80 and its concentric tube manipulator 60.

As a further feature, the guide pins 134 on the carriage assembly 130 and the guide apertures 136 on the front plate 84 of the transmission 80 can have predetermined cross-sectional shapes that limit or prevent certain transmissions 80 and their associated concentric tube manipulators 60 from being installed on certain carriage assemblies 130, i.e., at certain positions on the robotic surgical apparatus 20. This could be done to restrict the location of the tool cassettes 260 based on the types of tools they carry. For example, cross-sectional shapes or profiles, such as round, square, elliptical, polygonal (hexagonal, octagonal, etc.) can be implemented in configuring the guide pins 134 and guide apertures 136 so that only certain tool cassettes 260 can be positioned at certain locations on the support structure 150.

As another alternative, certain tool cassettes 260 can be universal cassettes configured to fit with any carriage assembly 130 so that they can be installed at any position on the support structure 150. To implement this, for example, the guide pins can be configured to have non-circular cross-sections, such as square or polygonal, with major dimensions that are the same. Tool cassettes 260 limited to certain positions would have to include guide apertures 136 that match the configuration of the guide pins. Universal tool cassettes 260 could include circular guide apertures 186 that have a diameter that matches the major dimension of the non-circular guide pins 184. This way, the universal tool cassettes 260 could be installed at any location, while the position specific tool cassettes would be limited to positions where the configuration of the guide pins 184 matches the configuration of the guide apertures 186.

We claim:

1. A surgical robot system comprising:
   a support structure for positioning relative to a patient, the support structure including a plurality of mounting structures;
   one or more robotic tool cassettes that are configured to interchangeably connect with any of the mounting structures, each tool cassette comprising a concentric tube manipulator and a transmission for operating the concentric tube manipulator;
   wherein the support structure further comprises a tube collector comprising a tube assembly associated with each of the mounting structures, the tube assemblies being configured to receive the concentric tube manipulators and guide the manipulators to extend along predetermined trajectories relative to each other.

2. The surgical robot system recited in claim 1, wherein the support structure comprises a main beam and wherein the mounting structures are connected to the main beam at positions spaced radially about the main beam.

3. The surgical robot system recited in claim 1, the mounting structures are configured to position the tool cassettes so that the concentric tube manipulators are directed toward a common location.

4. The surgical robot system recited in claim 1, wherein the tube collector is configured to receive and guide the concentric tube manipulators to exit the tube collector at trajectories that are substantially parallel to each other.

5. The surgical robot system recited in claim 4, wherein the tube collector is configured to redirect the concentric tube manipulators from angled trajectories at which the manipulators are received in the tube collector to substantially adjacent and parallel trajectories at which the manipulators exit the tube collector.

6. The surgical robot system recited in claim 1, wherein the tube collector is configured to direct the concentric tube manipulators to exit the tube collecting structure in a pattern configured so that the manipulators can extend through an ellipse having a major diameter of about 14 mm.

7. The surgical robot system recited in claim 1, wherein each concentric tube manipulator comprises a rigid outer tube and two curved inner tubes, the innermost tube carrying a surgical tool at its tip.

8. The surgical robot system recited in claim 1, wherein each of the tool cassettes have a form factor that is identical, the tool cassettes being interchangeably connectable to the mounting structure.

9. The surgical robot system recited in claim 1, wherein each mounting structure comprises a carriage assembly configured to receive a tool cassette, the mounting structure comprising a motor that is actuatable to move the carriage assembly linearly along the mounting structure to cause translational movement of the concentric tube manipulator of the tool cassette supported by the carriage assembly.

10. The surgical robot system recited in claim 9, wherein the carriage assembly comprises one or more guide pins configured to be received in corresponding guide apertures in the robotic tool cassette, and a handle that is actuatable to engage locking pins on the tool cassette to draw the tool cassette onto the carriage assembly with the guide apertures engaging the guide pins, and wherein the handle is configured to lock onto the locking pins to secure the tool cassette on the carriage assembly.

11. The surgical robot system recited in claim 10, wherein the guide pins and guide apertures have cross-sectional shapes selected such that a tool cassette having guide apertures of a matching cross-sectional shape can be installed only on carriage assemblies having guide pins configured to be received in those particular guide apertures.

12. The surgical robot system recited in claim 9, wherein the carriage assemblies and tool cassettes each have a form factor that is identical so that the tool cassettes are interchangeable on the carriage assemblies.

13. The surgical robot system recited in claim 1, wherein the concentric tube manipulators of each of the robotic tool cassettes is adapted to carry a tool at its distal end, such as grippers, surgical lasers, graspers, retractors, scissors, imaging tips, cauterization tips, ablation tips, wrists, curettes, morcelators, knives, scalpels, cameras, irrigation ports, and suction ports.

14. The surgical robot system recited in claim 1, wherein the tool cassettes and the concentric tube manipulators are configured to be sterilizable, and wherein the support structure is configured to receive a sterile curtain for providing a sterile barrier between the support structure and an operating room environment.

15. The surgical robot system recited in claim 1, wherein the tool cassettes are constructed of biocompatible and sterilizable components.

16. The surgical robot system recited in claim 1, further comprising one or more motor packs associated with the mounting structures and comprising one or more electric motors configured to supply rotational mechanical power to a tool cassette mounted thereon.

17. The surgical robot system recited in claim 16, wherein each tool cassette comprises a transmission for providing rotational and/or translational degrees of freedom of movement to the concentric tubes of its associated concentric tube manipulator, and wherein the motor pack includes an electric motor dedicated to each degree of freedom provided by the transmission.

18. The surgical robot system recited in claim 17, wherein the motor packs and the tool cassettes comprise couplings for automatically coupling the electric motors and the transmission.

19. The surgical robot system recited in claim 1, further comprising protective sleeves for protecting the concentric tube manipulators as they extend from the tool cassettes to the tube collector.

20. The surgical robot system recited in claim 19, further comprising a sliding port assembly configured to maintain the concentric tube manipulator centered within the protective sleeve, the sliding port assembly being connected to the concentric tube manipulator and being configured to arrest advancement of an outer concentric tube with its distal end proximate to and centered within an end portion of the collector tube so that the curved tubes of the concentric tube manipulator exit the tube collector from its center.

21. The surgical robot system recited in claim 1, further comprising markers applied to the concentric tubes of the concentric tube manipulator, the markers being configured to align in a predetermined pattern that is indicative of the concentric tube manipulator being in a home position.

22. The surgical robot system recited in claim 1, wherein the tube collector comprises an excluder opening through which the curved tubes of the concentric tube manipulator extend if installed in the tube collector in an improper orientation.

23. The surgical robot system recited in claim 1, wherein the tube collector comprises an opening through which the curved tubes of the concentric tube manipulator can extend if the tip of the curved tube moves over the opening, wherein the system is configured to have a homing mode in which the concentric tube manipulator is actuated translationally and rotationally within the collector tube while monitoring motor currents of motors actuating the concentric tube manipulator, a change in motor current being indicative of the curved tube tip engaging the opening, which is indicative of the location of the tip in the collector tube.

24. The surgical robot system recited in claim 1, further comprising a mechanical latch that locks the tool cassette in a retracted position to prevent re-use of the tool cassette.

* * * * *